(12) United States Patent
Briggs

(10) Patent No.: US 11,826,704 B2
(45) Date of Patent: *Nov. 28, 2023

(54) THERMO-RESPONSIVE SOLUTION, AND METHOD OF USE THEREFOR

(71) Applicant: Aquafortus Technologies Limited, Auckland (NZ)

(72) Inventor: Daryl Joseph Briggs, Auckland (NZ)

(73) Assignee: Aquafortus Technologies Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/246,440

(22) Filed: Apr. 30, 2021

(65) Prior Publication Data

US 2022/0193608 A1 Jun. 23, 2022

Related U.S. Application Data

(63) Continuation of application No. 16/338,076, filed as application No. PCT/NZ2017/050127 on Oct. 4, 2017, now Pat. No. 11,020,706.

(Continued)

(51) Int. Cl.
*B01D 61/00* (2006.01)
*C02F 1/44* (2023.01)

(Continued)

(52) U.S. Cl.
CPC ............ *B01D 61/005* (2013.01); *C02F 1/445* (2013.01); *C07C 49/08* (2013.01); *C07C 49/10* (2013.01);

(Continued)

(58) Field of Classification Search
CPC ......... A47K 11/023; F23G 5/04; C02F 1/445; C02F 2209/005; C02F 1/16;
(Continued)

(56) References Cited

U.S. PATENT DOCUMENTS 2,784,173 A * 3/1957 Carmack ................. C08G 75/23
528/211
3,077,500 A * 2/1963 Heinz ........................ B01J 31/08
568/388

(Continued)

FOREIGN PATENT DOCUMENTS

CA 1208134 A 7/1986
CN 1156418 A * 8/1997 ............ Y02P 20/584
(Continued)

OTHER PUBLICATIONS

English Translation of Fingeret et al Patent Publication CN1156418A, published Aug. 1997. (Year: 1997).*

(Continued)

*Primary Examiner* — Joseph W Drodge
(74) *Attorney, Agent, or Firm* — Nelson Mullins Riley & Scarborough LLP; Jane E. Remillard, Esq.; Cynthia L. Kanik

(57) ABSTRACT

The present invention relates to a thermo-responsive solution and in particular, a solution for use in an osmosis process that is suitable for separating or purifying solutes and or water from an aqueous solution on a large scale and under energy efficient conditions.

14 Claims, 17 Drawing Sheets

Related U.S. Application Data

(60) Provisional application No. 62/404,009, filed on Oct. 4, 2016.

(51) Int. Cl.
  *C07C 49/08* (2006.01)
  *C07C 49/10* (2006.01)
  *C07C 49/303* (2006.01)
  *C07C 211/05* (2006.01)

(52) U.S. Cl.
  CPC .......... *C07C 49/303* (2013.01); *C07C 211/05* (2013.01); *B01D 2311/103* (2013.01)

(58) Field of Classification Search
  CPC .... C02F 2303/16; C02F 2209/02; C02F 1/02; C02F 1/447; C02F 1/20; C02F 2103/08; C02F 1/44; C02F 2311/2626; C02F 2315/16; C02F 1/265; C02F 2101/10; C02F 2305/14; B01D 61/005; B01D 61/002; B01D 2311/2626; B01D 61/00; B01D 63/00; B01D 65/00; B01D 2311/04; B01D 2311/10; B01D 2311/103; B01D 2311/106; B01D 2311/12; B01D 2311/25; B01D 61/02; C07C 211/00; C07C 49/08; C07C 49/10; C07C 49/303; C07C 211/05; C01B 32/60; Y02A 20/131; Y02W 10/37; Y02P 20/10; C01D 3/06
  USPC ....... 210/637, 639, 644, 649, 650, 652, 177, 210/198.1, 195.1, 805; 252/181
  See application file for complete search history.

(56) References Cited

U.S. PATENT DOCUMENTS

| | | | |
|---|---|---|---|
| 3,130,156 A | 4/1964 | Neff | |
| 3,164,539 A | 1/1965 | Smith | |
| 5,346,620 A | 9/1994 | Hendrix et al. | |
| 5,705,074 A | 1/1998 | Brient | |
| 5,897,750 A * | 4/1999 | Berg | C07C 45/83 203/64 |
| 6,307,087 B1 | 10/2001 | Buchwald et al. | |
| 6,858,694 B2 | 2/2005 | Ohnishi et al. | |
| 6,858,964 B2 | 2/2005 | Masumoto et al. | |
| 7,560,029 B2 | 7/2009 | McGinnis | |
| 9,630,861 B2 | 4/2017 | Ikeda et al. | |
| 10,933,377 B2 | 3/2021 | Briggs et al. | |
| 11,020,706 B2 * | 6/2021 | Briggs | C02F 1/445 |
| 2002/0156295 A1 | 10/2002 | Buchwald et al. | |
| 2012/0043274 A1 | 2/2012 | Chi et al. | |
| 2013/0240444 A1 | 9/2013 | Jung et al. | |
| 2014/0076810 A1 | 3/2014 | Jessop et al. | |
| 2014/0158621 A1 | 6/2014 | Lee et al. | |
| 2014/0290854 A1 | 10/2014 | Parellada Llobet et al. | |
| 2014/0319056 A1 | 10/2014 | Fuchigami et al. | |
| 2015/0108061 A1 | 4/2015 | Chi et al. | |
| 2015/0166363 A1 | 6/2015 | Eyal et al. | |
| 2015/0273396 A1 | 10/2015 | Hancock et al. | |
| 2015/0360973 A1 | 12/2015 | Eyal et al. | |
| 2016/0023171 A1 | 1/2016 | Phillip et al. | |
| 2016/0158705 A1 | 6/2016 | Helm et al. | |
| 2016/0175777 A1 | 6/2016 | Ikeda et al. | |
| 2017/0354904 A1 | 12/2017 | Wilson et al. | |
| 2018/0015414 A1 * | 1/2018 | Hu | B01D 61/025 |
| 2019/0099718 A1 | 4/2019 | Briggs et al. | |
| 2020/0023316 A1 | 1/2020 | Briggs | |
| 2020/0308023 A1 | 10/2020 | Briggs et al. | |
| 2022/0185754 A1 | 6/2022 | Briggs et al. | |
| 2023/0043356 A1 | 2/2023 | Prakash et al. | |

FOREIGN PATENT DOCUMENTS

| | | |
|---|---|---|
| CN | 1717386 A | 1/2006 |
| CN | 104619649 A | 5/2015 |
| EP | 0117870 A1 | 9/1984 |
| WO | 2004050601 A2 | 6/2004 |
| WO | 2013175380 A1 | 11/2013 |
| WO | 2014089142 A1 | 6/2014 |
| WO | 2016094835 A1 | 6/2016 |
| WO | 2016133464 A1 | 8/2016 |
| WO | 2018/067019 A2 | 4/2018 |
| WO | 2019/070134 A2 | 4/2019 |

OTHER PUBLICATIONS

U.S. Appl. No. 17/436,439, filed Sep. 3, 2021, Daryl Joseph Briggs.
U.S. Appl. No. 17/599,284, filed Sep. 28, 2021, Chaitra Prakash.
U.S. Appl. No. 16/145,968, filed Sep. 28, 2018, Daryl Joseph Briggs, U.S. Pat. No. 10,933,377.
U.S. Appl. No. 16/338,076, filed Mar. 29, 2019, Daryl Joseph Brigg.
U.S. Appl. No. 16/753,263, filed Apr. 2, 2020, Daryl Joseph Brigg.
Alonso, I. , et al., "Thermodynamics of Ketone + Amine Mixtures. Part III. Volumetric and Speed of Sound Data at (293.15, 298.15, and 303.15) K for 2-Butanone + Aniline, + N-Methylaniline, or + Pyridine Systems," J. Chem. Eng. Data, vol. 55: 5400-5405 (2010).
Bahadur Alisha, S. et al., "Ultrasonic Studies on Binary Liquid Mixtures of Triethylamine with Carbitols at 308.15 K," Indian Journal of Advances in Chemical Science, vol. 5(3): 148-154 (2017).
González, J-A., et al. "Thermodynamics of ketone + amine mixtures. Part X. Excess molar enthalpies at 298.15 K for N,N,N-triethylamine + 2-alkanone systems. Characterization of tertiary amine + 2-alkanone, and of amino-ketone + n-alkane mixtures in terms of DISQUAC," Fluid Phase Equilibria, vol. 356: 117-125 (2013).
International Preliminary Report on Patentability, PCT/NZ2017/050127, dated Apr. 4, 2019, 6 pages.
International Search Report and Written Opinion, PCT/NZ2017/050127, dated Jan. 22, 2019, 8 pages.
Reddy, K.C. et al., "Ultrasonic Behaviour of Binary Liquid Mixtures Containing Trie thy lamine, Part 1," Trans. Faraday Soc., vol. 58: 2352-2357 (1962).

* cited by examiner

Cyclohexanone

THERMO-RESPONSIVE SOLUTION, AND METHOD OF USE THEREFOR

CROSS-REFERENCE TO RELATED APPLICATIONS

This application is a continuation of U.S. application Ser. No. 16/338,076, filed Mar. 29, 2019, which is a 35 U.S.C. 371 national stage filing of International Application No. PCT/NZ2017/050127, filed Oct. 4, 2017, which claims priority to U.S. Provisional Application No. 62/404,009, filed Oct. 4, 2016. The contents of the aforementioned applications are each hereby incorporated by reference.

FIELD OF THE INVENTION

The present disclosure relates to a thermo-responsive solution and in particular, a solution suitable for use in an osmosis process that is suitable for separating or purifying solutes and or water from an aqueous solution on a large scale and under energy efficient conditions.

BACKGROUND OF THE INVENTION

U.S. Pat. No. 3,130,156 to Neff is directed to a forward osmosis desalination process, which describes the use of a 2 molar solution of ammonium bicarbonate being used to draw water from seawater across a semi-permeable membrane. According to Neff, the dilute solution obtained that contains the water and ammonium bicarbonate mixture is then heated to convert the ammonium bicarbonate solute into its constituent gases of ammonia and carbon dioxide. The gases are then released from the solution to leave behind purified water. It is to be appreciated that considerable amounts of energy are required to vaporise the gases. Additionally, only relatively small quantities of water are purified from a large volume of seawater meaning that the ratio of energy input required in the process to the yield of purified water obtained is low. This means that this process is not suitable for large scale applications.

The Neff concept was further developed and refined by McGinnis, as described in U.S. Pat. No. 7,560,029, into a more energy efficient desalination process that is scalable. The principle of adding a mixture of ammonia and carbon dioxide with resultant aqueous species of ammonium carbonate, ammonium bicarbonate and ammonium carbamate to adjust the osmotic equilibrium in a forward osmosis process is used in McGinnis. Furthermore, the resultant separated water was purified by heating to drive off ammonia and carbon dioxide. The water separated in this process will still be tainted slightly by ammonia and its presence means that an odour will be detectable.

Jessop et. al. in US 2014/0076810 describes a switchable water or aqueous solution and its use. The switchable water or aqueous solution is formed by adding an ionisable additive comprising an ionisable functional group having at least one nitrogen atom. The additive is further described as a monoamine, a diamine, a triamine, a tetramine or a polyamine, such as a polymer or a biopolymer. The switchable water or aqueous solution is capable of reversibly switching between an initial ionic strength and an increased ionic strength by using a trigger, such as bubbling with $CO_2$, $CS_2$ or COS or treatment with Bronsted acids. The switchability of the water or aqueous solution allows for the control of solubility or insolubility of various hydrophobic liquids or solvents in the water or aqueous solution. This provides a means of separating moderately hydrophobic solvents from the switchable water. One of the difficulties with the Jessop work is that is difficult to disassociate the $CO_2$ from the amine to achieve the switchable water. Trace amounts of $CO_2$ and amine can remain solubilised in the draw solution and heating and stripping and the kinetics of recovery are slow—of the order of hours to minutes.

US 2013/0240444 to Jung et. al. describes the use of a temperature sensitive oligomer, wherein the oligomer has a repeating unit of —C(=O)N(R)$_2$ (ie an amide functional group) where each R may be linear or branched or together they form a nitrogen containing heterocycle for use as a draw solution. The oligomer may be used in an osmotic draw solution for separating out a solute in an aqueous medium. The draw solute is recoverable by a phase separation at a temperature greater than or equal to a lower critical solution temperature. The lower critical solution temperature (LCST) is the critical temperature below which the components of a mixture are miscible. The word lower indicates that the LCST is a lower bound to a temperature interval of partial miscibility, or miscibility for certain compositions only. In other words, the thermosensitive nature of the oligomer exhibits sharply decreased water solubility in response to a small increase in temperature leading to precipitation. At a temperature lower than the LCST the oligomer or polymers therefrom may be easily dissolved in water, but at temperatures higher than or equal to the LCST the hydrophilicity of the oligomer or polymers therefrom may decrease and the hydrophobic interactions predominate. One of the problems with oligomers and polymers is that they are relatively large molecules and large molecules create a diffusion concentration polarisation which lowers effective osmotic potential of the forward osmosis system by making the draw solution less drawable. Relatively large molecules and polymers also rely on precipitation mechanisms rather than emulsification to recover the draw solute, necessitating a secondary filtration mechanism that increases system cost and complexity.

US 2014/0158621 to Lee at al. also describes a thermo-responsive draw solute based on a compound or material including at least one amide functional group, or a carboxylic acid functional group, that can be applied to water desalination and purification based on forward osmosis. Similar to Jung above, Lee also describes the use and applicability of an amide type functional group in a thermo-responsive draw solution and the reliance on the LCST to effect phase separation of a solute from the draw solution in a forward osmosis application. One of the problems with oligomers and polymers is that they are relatively large molecules and large molecules create a diffusion concentration polarisation which lowers effective osmotic potential of the forward osmosis system by making the draw solution less drawable. Relatively large molecules and polymers also rely on precipitation mechanisms rather than emulsification to recover the draw solute, necessitating a secondary filtration mechanism that increases system cost and complexity.

U.S. Pat. No. 6,858,694 to Onishi et. al describes a stimuli responsive polymer derivative which exhibits both a lower critical solution temperature and an upper critical solution temperature (UCST), causing its reversible dissolution and precipitation depending on the hydrogen ion concentration. The polymers described in '694 also rely on an amide type functional group that are described as exhibiting keto-enol tautomerisation. One of the problems with polymers is that they are relatively large molecules and large molecules create a diffusion concentration polarisation which lowers effective osmotic potential of the forward osmosis system by making the draw solution less drawable.

US 2016/0175777 to Ikeda et al. describes an improved forward osmosis apparatus employing a draw solution that utilises an anion and cation source. In particular the anions are derived from $CO_2$, ie a substance that generates anions when dissolved in water, such as carbonic acid anions and or hydrogen carbonate anions. The cation source is an amine compound, which generates cations when dissolved in water. The draw solution is broadly described as a solution having a cation source and an anion source. The physical separation of the $CO_2$ relies on gaseous separation, which is a relatively complex and energy inefficient process. Their preferred amines are fully miscible and have a molecular weight of less than 74.

Despite the efforts described above the draw solutions described remain largely unsatisfactory, they either rely on expensive components, require considerable energy levels to recover the draw solution or rely on large molecules that are inefficient from a draw solution perspective. It is an object of the present invention to provide a solution that overcomes these difficulties or to at least provide a useful alternative.

SUMMARY OF THE INVENTION

The present invention is directed to a thermo-responsive solution and its use in osmotic processes.

In one aspect the present invention provides a thermo-responsive osmotic solution having a lower critical solution temperature in a solvent suitable for use in osmosis comprising:
  a) at least one tertiary amine containing compound; and
  b) at least one enolisable carbonyl;
wherein in use at least one of the base or the at least one enolisable carbonyl is immiscible with water at or above 20 degrees Celsius and at 1 atmosphere.

In a further aspect the present invention provides a thermo-responsive osmotic solution having a lower critical solution temperature in a solvent suitable for use in osmosis comprising:
  a) at least one tertiary amine containing compound; and
  b) at least one enolisable carbonyl of Formula I,

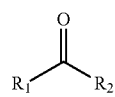

Formula I wherein
  c) $R_1$ and $R_2$ are independently selected from a —$C_1$-$C_7$ alkyl or a —$C_3$-$C_7$ monocyclic; or
  d) one of $R_1$ or $R_2$ is selected from a —O—($C_1$-$C_7$ alkyl) and the other is selected from a —$C_1$-$C_7$ alkyl, or
  e) $R_1$ and $R_2$ together, with the carbonyl of Formula I, form
    1) a 3-15 membered monocyclic ketone or
    2) a 3-15 membered monocyclic heterocyclic ketone; or
    3) acetophenone; and
wherein in use at least one of the base or the at least one enolisable carbonyl is immiscible with water at or above 20 degrees Celsius and at 1 atmosphere.

In another aspect the present invention provides a method for separating a first solution including one or more solvents, using a thermo-responsive solution as defined above, the method comprising:

1) bringing the first solution into contact with a semi-permeable membrane;
  2) allowing one or more solvents in the first solution to flow through the semi-permeable membrane from the first solution into the thermo-responsive solution by osmosis to form a second solution, wherein the thermo-responsive solution is at a higher osmotic concentration than the first solution;
  3) raising the temperature of the second solution to or above the lower critical solution temperature of the thermo-responsive solution to cause the thermo-responsive solution to become immiscible with the one or more solvents from the first solution that have passed through the semi-permeable membrane; and
  4) separating the one or more solvents that have passed through the semipermeable membrane from the immiscible thermo-responsive solution.

In another aspect the present invention provides a method for separating a first solution including one or more solvents, using a thermo-responsive solution as defined above, the method comprising:
  1) bringing the first solution into contact with a semi-permeable membrane;
  2) allowing one or more solvents in the first solution to flow through the semi-permeable membrane from the first solution into the thermo-responsive solution by osmosis to form a second solution, wherein the thermo-responsive solution is at a higher osmotic concentration than the first solution;
  3) adjusting the lower critical solution temperature of the thermo-responsive solution to cause the thermo-responsive solution to become immiscible with the one or more solvents from the first solution that have passed through the semi-permeable membrane; and
  4) separating the one or more solvents that have passed through the semipermeable membrane from the immiscible thermo-responsive solution.

In one embodiment the lower critical solution temperature of the thermo-responsive solution is adjusted by adding one or more tertiary amine containing compounds as defined, or by adding or more enolisable carbonyls as defined above or by adding combinations of the one or more tertiary amine containing compounds with the one or more enolisable compounds.

The foregoing brief summary broadly describes the features and technical advantages of certain embodiments of the present invention. Further technical advantages will be described in the detailed description of the invention and examples that follows.

Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to limit the invention's scope.

BRIEF DESCRIPTION OF THE DRAWINGS

FIG. 4A-FIG. 4C shows a series of photos showing the observable differences of a triethylamine plus 2-butanone in water solution demonstrating a change in physical properties of the solution over a temperature range. FIG. 4A shows that at 26.65° C. the base, ketone and water mixture is miscible. FIG. 4B shows that at 26.89° C. the base, ketone and water mixture has become turbid in appearance as a result of the base and ketone mixture becoming an emulsion with water. FIG. 4C shows that at 27.05° C. the base and ketone mixture are immiscible with water.

FIG. 5A shows that at 15.21° C. the base, ketone and water mixture is miscible. FIG. 5B shows that at 15.38° C. the base, ketone and water mixture has become turbid in appearance as a result of the base and ketone mixture becoming an emulsion with water. FIG. 5C shows that at 18.33° C. the base and ketone mixture are immiscible with water.

DETAILED DESCRIPTION OF THE INVENTION

Figure 1:
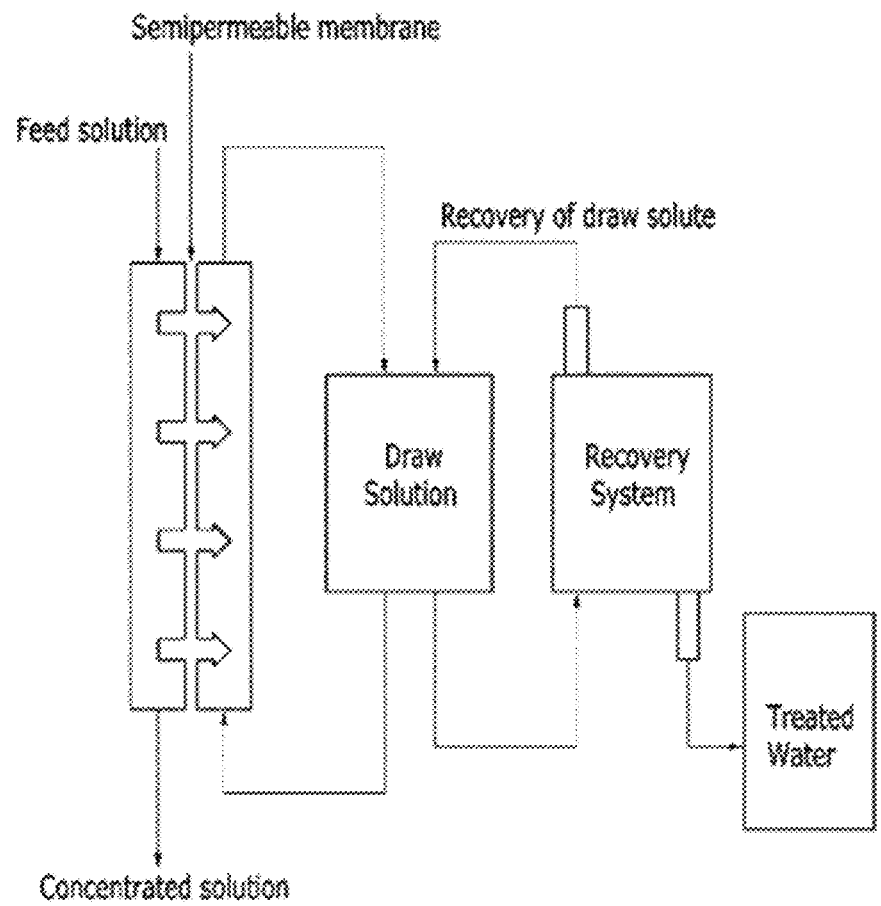
FIG. 1 shows schematically an osmotic separation process.

The following description sets forth numerous exemplary configurations, parameters, and the like. It should be recognised, however, that such description is not intended as a limitation on the scope of the present invention, but is instead provided as a description of exemplary embodiments.

Definitions

In each instance herein, in descriptions, embodiments, and examples of the present invention, the terms "comprising", "including", etc., are to be read expansively, without limitation. Thus, unless the context clearly requires otherwise, throughout the description and the claims, the words "comprise", "comprising", and the like are to be construed in an inclusive sense as opposed to an exclusive sense, that is to say in the sense of "including but not limited to".

The term "osmosis" is to be understood as a membrane based separation process that relies on the semipermeable character of a semi-permeable membrane to remove dissolved solutes or to effect separation of a solvent from dissolved solutes, and wherein the driving force for separation is osmotic pressure. The term "osmotic solution" means a solution that creates osmotic pressure across the semi-permeable membrane.

The term "about" or "approximately" usually means within 20%, more preferably within 10%, and most preferably still within 5% of a given value or range. Alternatively, the term "about" means within a log (i.e., an order of magnitude) preferably within a factor of two of a given value.

As used herein, the term "$C_1$-$C_7$ alkyl" refers to a fully saturated branched or unbranched hydrocarbon moiety, which may be a straight or a branched chain of a particular range of 1-7 carbons. Preferably the alkyl comprises 1 to 7 carbon atoms, or 1 to 4 carbon atoms. Representative examples of $C_1$-$C_7$ alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, and the like. For example, the expression $C_1$-$C_4$-alkyl includes, but is not limited to, methyl, ethyl, propyl, butyl, isopropyl, tert-butyl and isobutyl. In one embodiment the $C_1$-$C_7$ alkyl group may be substituted with one or more of the following groups: -halo, —OH, —CN, —NO$_2$, —C≡CH, —SH, —$C_1$-$C_7$ alkyl, —($C_1$-$C_7$ alkyl)-OH, —NH$_2$, —NH($C_1$-$C_7$ alkyl), —N($C_1$-$C_7$ alkyl)$_2$, —O($C_1$-$C_7$ alkyl), —C(O)—O(—$C_1$-$C_7$ alkyl), —C(O)OH; —C(O)—H, or —C(O)—($C_1$-$C_7$ alkyl).

The term "$C_3$-$C_7$ monocyclic" as used herein is a 3-, 4-, 5-, 6-, or 7-membered saturated or unsaturated monocyclic ring. Representative $C_3$-$C_7$ monocyclic groups include, but are not limited to, cyclopropyl, cyclobutyl, cyclopentyl, cyclohexyl, phenyl and cycloheptyl. In one embodiment, the $C_3$-$C_7$ monocyclic cycloalkyl group may be substituted with one or more of the following groups: -halo, —OH, —CN, —NO$_2$, —C≡CH, —SH, —$C_1$-$C_7$ alkyl, —($C_1$-$C_7$ alkyl)-OH, —NH$_2$, —NH($C_1$-$C_7$ alkyl), —N($C_1$-$C_7$ alkyl)$_2$, —O($C_1$-$C_7$ alkyl), —C(O)—O(—$C_1$-$C_7$ alkyl), —C(O)OH; —C(O)—H, or —C(O)—($C_1$-$C_7$ alkyl).

The term "3- to 15-membered monocyclic ketone" refers to a 3- to 15-membered non-aromatic monocyclic ring system containing a ketone functional group. Representative examples of a 3- to 15-membered monocyclic ketone include, but are not limited to cyclopropanone, cyclobutanone, cyclopentanone, cyclohexanone, cycloheptanone, cyclooctanone, cyclononanone, cyclodecanone, cycloundecanone, cyclododecanone, cyclotridecanone; cyclotetradecanone and cyclopentadecanone.

In one embodiment, the 3- to 15-membered monocyclic ketone may be substituted with one or more of the following groups -halo, —OH, —CN, —NO$_2$, —C≡CH, —SH, —$C_1$-$C_7$ alkyl, —($C_1$-$C_7$ alkyl)-OH, —NH$_2$, —NH($C_1$-$C_7$ alkyl), —N($C_1$-$C_7$ alkyl)$_2$, —O($C_1$-$C_7$alkyl), —C(O)—O(—$C_1$-$C_7$ alkyl), —C(O)OH; —C(O)—H, or —C(O)—($C_1$-$C_7$ alkyl).

The term "3- to 15-membered monocyclic heterocyclic ketone" refers to: (i) a 3- or 4-membered non-aromatic monocyclic cycloalkyl in which 1 of the ring carbon atoms has been replaced with an N, O or S atom; or (ii) a 5- to 15-membered non-aromatic monocyclic cycloalkyl in which 1-4 of the ring carbon atoms have been independently replaced with a N, O or S atom. Representative examples of a 3- to 15-membered monocyclic heterocyclic ketone having one N, O or S atom include, but are not limited to oxiran-2-one, thiiran-2-one, oxetan-2-one, oxetan-3-one, azetidin-3-one, thietan-2-one, thietan-3-one, dihydrofuran-2(3H)-one, dihydrofuran-3(2H)-one, pyrrolidin-3-one, dihydrothiophen-3(2H)-one, dihydrothiophen-2(3H)-one, tetrahydro-2H-pyran-2-one, dihydro-2H-pyran-3(4H)-one, dihydro-2H-pyran-4(3H)-one, piperidin-3-one, piperidin-4-one, tetrahydro-2H-thiopyran-2-one, dihydro-2H-thiopyran-3(4H)-one, dihydro-2H-thiopyran-4(3H)-one, oxepan-2-one, oxepan-3-one, oxepan-4-one, thiepan-2-one, thiepan-3-one, thiepan-4-one, azepan-3-one, azepan-4-one, oxocan-2-one, oxocan-3-one, oxocan-4-one, oxocan-5-one, thiocan-2-one, thiocan-3-one, thiocan-4-one, thiocan-5-one, azocan-3-one, azocan-3-one, azocan-4-one, azocan-5-one, azonan-3-one, azonan-4-one, azonan-5-one, oxonan-2-one, oxonan-3-one, oxonan-4-one, oxonan-5-one, thionan-2-one, thionan-3-one, thionan-4-one, thionan-5-one, oxacycloundecan-2-one, oxacycloundecan-3-one, oxacycloundecan-4-one, oxacycloundecan-5-one, oxacycloundecan-6-one, azacycloundecan-3-one, azacycloundecan-4-one, azacycloundecan-5-one, azacycloundecan-6-one, thiacycloundecan-2-one, thiacycloundecan-3-one, thiacycloundecan-4-one, thiacycloundecan-5-one, thiacycloundecan-6-one, oxacyclododecan-2-one, oxacyclododecan-3-one, oxacyclododecan-4-one, oxacyclododecan-5-one, oxacyclododecan-6-one, oxacyclododecan-7-one, azacyclododecan-3-one, azacyclododecan-4-one, azacyclododecan-5-one, azacyclododecan-6-one, azacyclododecan-7-one, thiacyclododecan-2-one, thiacyclododecan-3-one, thiacyclododecan-4-one, thiacyclododecan-5-one, thiacyclododecan-6-one, thiacyclododecan-7-one, oxacyclotridecan-2-one, oxacyclotridecan-3-one, oxacyclotridecan-4-one, oxacyclotridecan-5-one, oxacyclotridecan-6-one, oxacyclotridecan-7-one, azacyclotridecan-3-one, azacyclotridecan-4-one, azacyclotridecan-5-one, azacyclotridecan-6-one, azacyclotridecan-7-one, thiacyclotridecan-2-one, thiacyclotridecan-3-one, thiacyclotridecan-4-one, thiacyclotridecan-5-one, thiacyclotridecan-6-one, thiacyclotridecan-7-one, oxacyclotetradecan-2-one, oxacyclotetradecan-3-one, oxacyclotetradecan-4-one, oxacyclotetradecan-5-one, oxacyclotetradecan-6-one, oxacyclotetradecan-7-one, oxacyclotetradecan-8-one, azacyclotetradecan-3-one, azacyclotetradecan-4-one, azacyclotetradecan-5-one, azacyclotetradecan-6-one, azacyclotetradecan-7-one, azacyclotetradecan-8-one, thiacyclotetradecan-2-one, thiacyclotetradecan-3-one, thiacyclotetradecan-4-one, thiacyclotetradecan-5-one, thiacyclotetradecan-6-one, thiacyclotetradecan-7-one, thiacyclotetradecan-8-one, oxacyclopentadecan-2-one, oxacyclopentadecan-3-one, oxacyclopentadecan-4-one, oxacyclopentadecan-5-one, oxacyclopentadecan-6-one, oxacyclopentadecan-7-one, oxacyclopentadecan-8-one, azacyclopentadecan-3-one, azacyclopentadecan-4-one, azacyclopentadecan-5-one, azacyclopentadecan-6-one, azacyclopentadecan-7-one, azacyclopentadecan-8-one, thiacyclopentadecan-2-one, thiacyclopentadecan-3-one, thiacyclopentadecan-4-one, thiacyclopentadecan-5-one, thiacyclopentadecan-6-one, thiacyclopentadecan-7-one, thiacyclopentadecan-8-one. In one embodiment, the 3- to 15-membered monocyclic heterocyclic ketone group may be substituted with one or more of the following groups -halo, —OH, —CN, —NO$_2$, —C≡CH, —SH, —C$_1$-C$_6$ lower alkyl, —(C$_1$-C$_7$ alkyl)-OH, —NH$_2$, —NH(C$_1$-C$_7$ alkyl), —N(C$_1$-C$_7$ alkyl)$_2$, —O(C$_1$-C$_7$ alkyl), —C(O)—O(—C$_1$-C$_7$ alkyl), —C(O)OH; —C(O)—H, or —C(O)—(C$_1$-C$_7$ alkyl). For the avoidance of doubt, the 3-5 membered monocyclic heterocyclic ketone does not include any amide groups where the ketone enolisable carbonyl group is adjacent a N atom in the cyclic structure.

The term "halo" as used herein refers to —F, —Cl, —Br or —I.

The term immiscible as used herein, means not fully miscible or capable of forming a single continuous phase with the solvent phase.

The term "an enolisable carbonyl" means a compound that has one or more carbonyl functional groups and wherein at least one of the carbonyl functional groups has alpha hydrogens (H$_\alpha$) that may be removed by a base to form an enolate and then an enol as shown in the reaction scheme below.

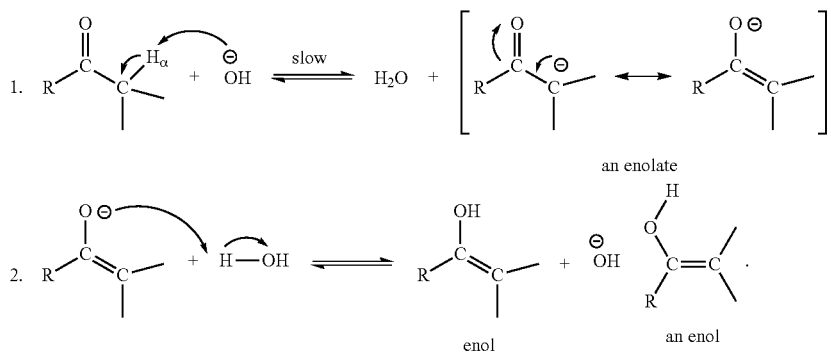

It is to be understood that the term enolisable carbonyl as used in the specification does not include a compound having solely an aldehyde functional group, a compound having solely a carboxylic acid functional group, a compound having solely an amide functional group, a compound having solely an acyl halide functional group or acetylacetone.

The term enolisable carbonyl, without limitation includes one or more of the following: acetone, acetophenone, methylethylketone (2-butanone), cyclohexanone, cyclopentanone, 2-propanone, 2-pentanone, 3-pentanone, 4-methyl-2-pentanone, 2-octanone and 3-methyl-2-butanone. In a preferred embodiment the term enolisable carbonyl includes one or more of the following acetone, acetophenone, cyclohexanone, cyclopentanone, 2-propanone, 2-pentanone, 3-pentanone, 4-methyl-2-pentanone, 2-octanone and 3-methyl-2-butanone.

The term "tertiary amine containing compound" is preferably one that is a Lewis base. If the base is a Lewis base, it is envisaged that a Lewis adduct may be formed with the enolisable carbonyl. In one embodiment it is preferred that the tertiary amine containing compound is immiscible with water at or above 20 degrees Celsius under one standard atmosphere of pressure. The solution may include a combination of more than one tertiary amine containing compound. The tertiary amine containing compound can be aliphatic, conjugated, asymmetric or cyclic.

Examples of suitable tertiary amines include the following:

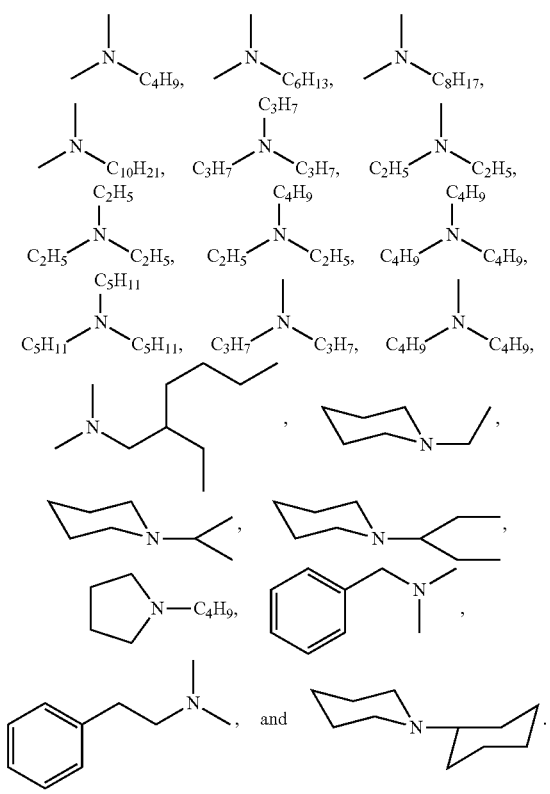

In one embodiment the base is selected from a —N($C_1$-$C_7$ alkyl)$_3$. In another embodiment the base is selected from a —N($C_1$-$C_4$ alkyl)$_3$. In yet a further embodiment the base is —N($C_2$ alkyl)$_3$ (triethylamine).

It will be appreciated that the above listed amines are simple enough for production on an industrial scale.

The term "thermo-responsive solution" means a solution that exhibits a drastic and discontinuous change of its solubility with temperature.

The term "lower critical solution temperature" (LCST) means the critical temperature below which the properties (optical, conductivity and/or pH) of the solution begin to change on the continuum to the components of the solution becoming miscible.

The present invention is directed to a thermo-responsive osmotic solution and its use in osmosis processes. The inventor has conducted research into looking for alternative thermo-responsive solutions that are likely to be readily scalable on an industrial scale, whilst also providing very efficient diffusion and osmotic potential properties both cost and energy efficiently. The inventor has determined that a suitable thermo-responsive osmotic solution having a lower critical solution temperature in a solvent for use in osmosis comprises:

b) at least one tertiary amine containing compound; and
c) at least one enolisable carbonyl of Formula I,

Formula I wherein
d) $R_1$ and $R_2$ are independently selected from a —$C_1$-$C_7$ alkyl or a —$C_3$-$C_7$ monocyclic or a -phenyl; or
e) one of $R_1$ or $R_2$ is selected from a —O—($C_1$-$C_7$ alkyl) and the other is selected from a —$C_1$-$C_7$ alkyl, or
f) $R_1$ and $R_2$ together, with the carbonyl of Formula I, form
   1) a 3-15 membered monocyclic ketone or
   2) a 3-15 membered monocyclic heterocyclic ketone; or
   3) acetophenone; and
wherein in use at least one of the base or the at least one enolisable carbonyl is immiscible with water at 20 degrees Celsius and at 1 atmosphere.

In one embodiment, $R_1$ and $R_2$ of Formula I are independently selected from a —$C_1$-$C_7$ alkyl. In another embodiment $R_1$ and $R_2$ are independently selected from methyl and ethyl. In one embodiment the enolisable carbonyl is selected from 2-butanone, acetone, isobutylketone. In one embodiment the solution includes a combination of more than one enolisable carbonyl of Formula I. In one embodiment the combination of enolisable carbonyls of Formula I includes the following combinations;
  A. 2 butanone and 2-propanone;
  B. 2-propanone and cyclohexanone;
  C. 2 butanone and cyclohexanone;
  D. 2 propanone, 2 butanone and cyclohexanone;
  E. 2-propanone and 2-pentanone;
  F. Cyclopentanone and acetophenone;
  G. Cyclopentanone and 2-octanone;
  H. Cyclopentanone and 4methyl-2-pentanone;
  I. 2-butanone, cyclopentanone and 2-propanone; and
  J. 2-propanone, 3-pentanone and 3-methyl-2-butanone.

In one embodiment the solution includes a combination of more than one tertiary amine containing compound of Formula I. In one embodiment the combination of tertiary amine containing compounds includes the following combinations;
  K. Triethylamine and 1-ethylpiperidine;
  L. Triethylamine and diethylmethylamine;
  M. Triethylamine, diethylmethylamine and 1-ethylpiperidine; and
  N. Triethylamine, diethylmethylamine and dimethylbenzylamine;

In one embodiment $R_1$ of Formula I is selected from a —$C_1$-$C_7$ alkyl and $R_2$ is selected from a —O—($C_1$-$C_7$ alkyl). In a further embodiment the enolisable carbonyl is selected from ethyl formate or methyl formate.

In a further embodiment wherein $R_1$ and $R_2$ of Formula I together form a cyclic system selected from a 3-15 membered monocyclic ketone or a monocyclic ester. In one embodiment the enolisable carbonyl is selected from cyclohexanone or tetrahydro-2H-pyran-2-one.

It is to be appreciated that when $R_1$ and $R_2$ together form a cyclic system, the cyclic system may be further substituted with one or more substituents selected from -halo, —OH, —CN, —$NO_2$, —C≡CH, —SH, —$C_1$-$C_7$ alkyl, —($C_1$-$C_7$ alkyl)-OH, —$NH_2$, —NH($C_1$-$C_7$ alkyl), —N($C_1$-$C_7$ alkyl)$_2$, —O($C_1$-$C_7$ alkyl), —C(O)—O(—$C_1$-$C_7$ alkyl), —C(O)OH; —C(O)—H, or —C(O)—($C_1$-$C_7$ alkyl) or the like.

Figure 7A:
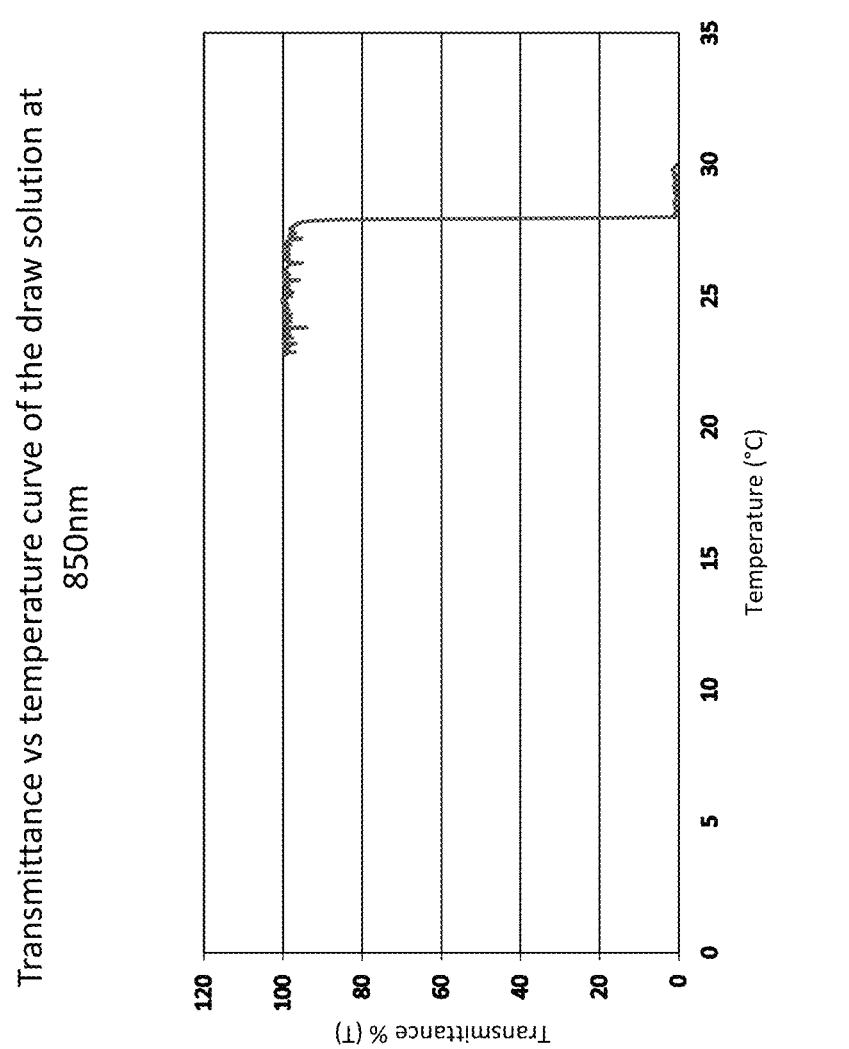
FIG. 7A shows a plot of the transmittance % versus the temperature curve of a draw solution of TEA:MEK:water (0.5:1.0:5.0 respectively).
Figure 7B:
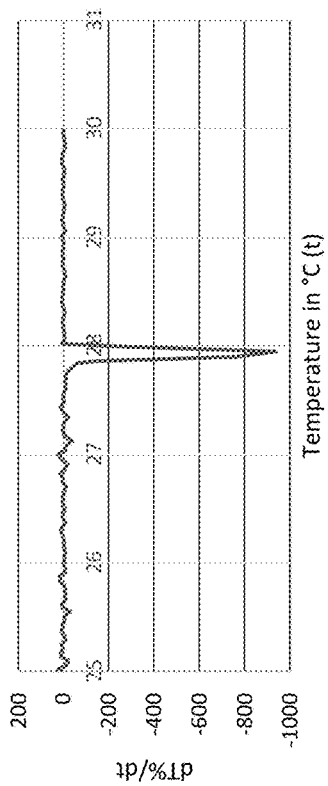
FIG. 7B and FIG. 7C, respectively, show the first and second derivative plots of the transmittance curve shown in FIG. 7A.
Figure 7C:
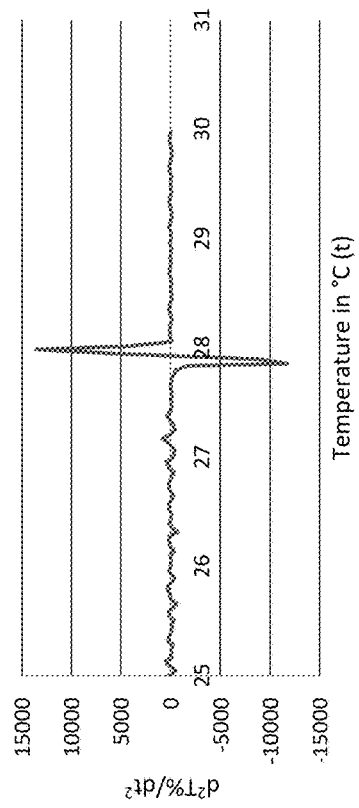
Figure 8:
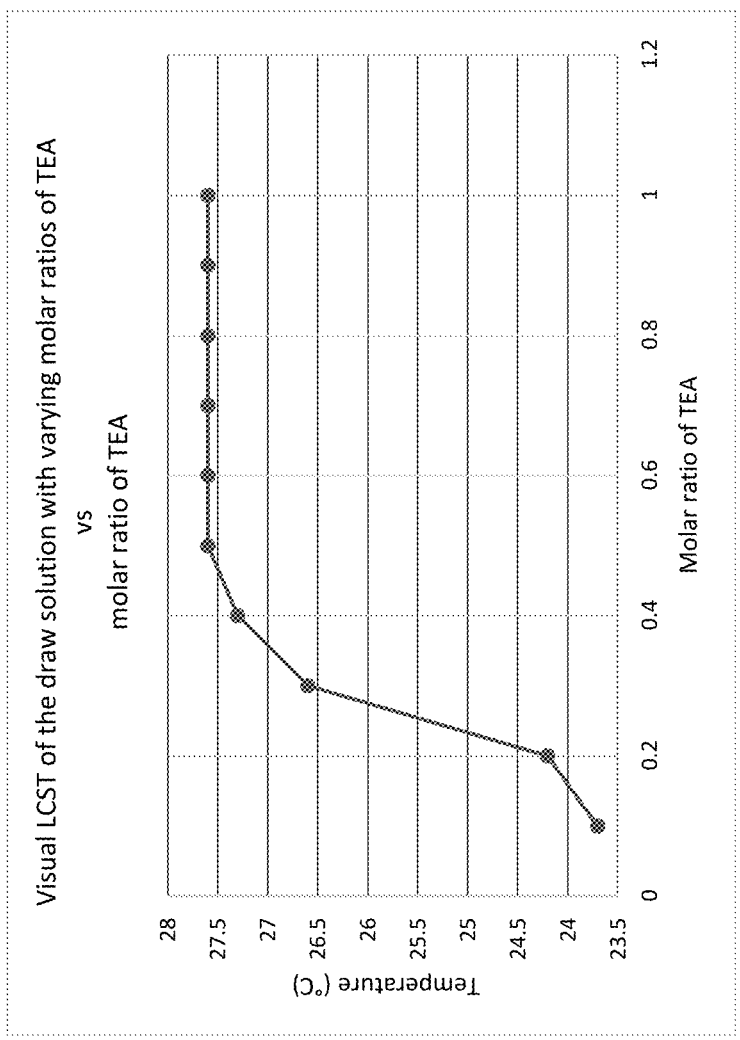
FIG. 8 shows a plot of the visual LCST of a draw solution with varying molar ratios of TEA in the draw solution versus the molar ratio of TEA.
Figure 9:
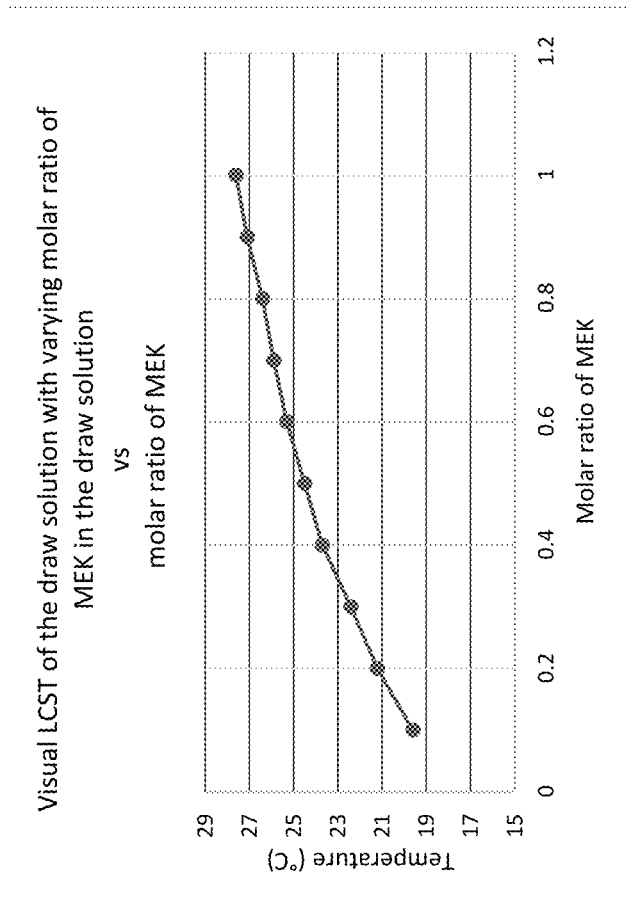
FIG. 9 shows a plot of the visual LCST of a draw solution with varying molar ratios of MEK in the draw solution versus the molar ration of MEK.

It is to be appreciated that the molar ratio of the base to the enolisable carbonyl of Formula I may vary widely and may be from about 1:99 or 99:1; or from about 1:50 or 50:1 or from about 1:10 or 10:1 or from about 1:5 or 5:1 or from about 1:3 or from about 3:1 or from about 1:2 or from about 2:1. In a preferred embodiment the molar ratio is about 1:1. A chemistry technician would be able to routinely determine the most suitable molar ratio depending on the purpose for which the thermo-responsive solution is to be employed. A range of molar ratios for various thermo-responsive solutions are shown in FIGS. 7 to 9.

In one embodiment the solvent is water.

In a further aspect there is provided an osmotic process or method for separating a first solution including one or more solvents, using a thermo-responsive solution as defined above. The method comprises:

1) bringing a first solution into contact with a semi-permeable membrane;
2) allowing one or more solvents in the first solution to flow through the semi-permeable membrane from the first solution into the thermo-responsive solution by osmosis to form a second solution, wherein the thermo-responsive solution is at a higher osmotic concentration than the first solution;
3) raising the temperature of the second solution to or above the lower critical solution temperature of the thermo-responsive solution to cause the thermo-responsive solution to become immiscible with the one or more solvents from the first solution that have passed through the semi-permeable membrane; and
4) separating the one or more solvents that have passed through the semipermeable membrane from the immiscible thermo-responsive solution.

In another aspect the present invention provides a method for separating a first solution including one or more solvents, using a thermo-responsive solution as defined above, the method comprising:

1) bringing the first solution into contact with a semi-permeable membrane;
2) allowing one or more solvents in the first solution to flow through the semi-permeable membrane from the first solution into the thermo-responsive solution by osmosis to form a second solution, wherein the thermo-responsive solution is at a higher osmotic concentration than the first solution;
3) adjusting the lower critical solution temperature of the thermo-responsive solution to cause the thermo-responsive solution to become immiscible with the one or more solvents from the first solution that have passed through the semi-permeable membrane; and
4) separating the one or more solvents that have passed through the semipermeable membrane from the immiscible thermo-responsive solution.

In one embodiment the lower critical solution temperature of the thermo-responsive solution is adjusted by adding one or more tertiary amine containing compounds as defined, or by adding or more enolisable carbonyls as defined above or by adding combinations of the one or more tertiary amine containing compounds with the one or more enolisable compounds.

It is to be appreciated that the first solution in the above aspects may include one or more dissolved solutes. In a further embodiment the first solution is selected from seawater, brackish water, industrial water waste streams, compromised water sources, sewage, wastewater liquors, digestates, food & beverage processing effluents, grey water, fruit juices, vegetable juices, milk, produced waters, leachates, flue gas scrubber discharge or the like.

EXAMPLES

The examples described herein are provided for the purpose of illustrating specific embodiments of the invention and are not intended to limit the invention in any way. Persons of ordinary skill can utilise the disclosures and teachings herein to produce other embodiments and variations without undue experimentation. All such embodiments and variations are considered to be part of this invention.

Example 1

Figure 2:
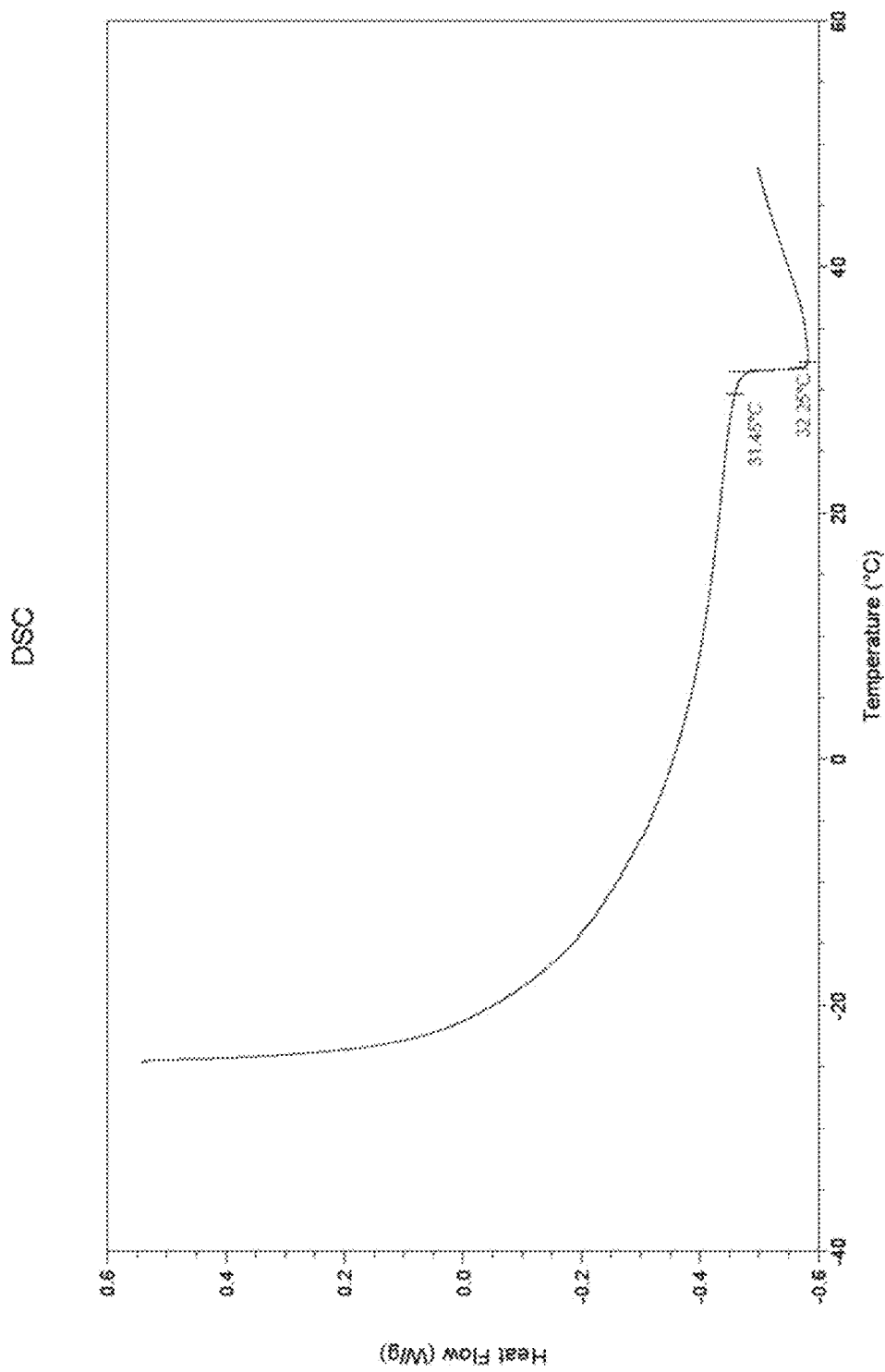
FIG. 2 shows the differential scanning calorimetry (DSC) analysis for a triethylamine plus acetone in water solution demonstrating a change of enthalpy at 32.25° C., which coincides with the observed solubility/polarity shift.

In a first example, the inventor took equal molar ratios of acetone as the enolisable carbonyl plus triethylamine as the base in a volume of water in a test tube. A DSC scan of that solution showed that there was a thermo-responsive point at 32.25° C. at which the lower critical solution temperature was reached—see FIG. 2. It was observed that close to that point the solution went from a miscible mixture of acetone/tertiary amine in water through an emulsion to an immiscible mixture of acetone/tertiary amine in water.

Example 2

Figure 3:
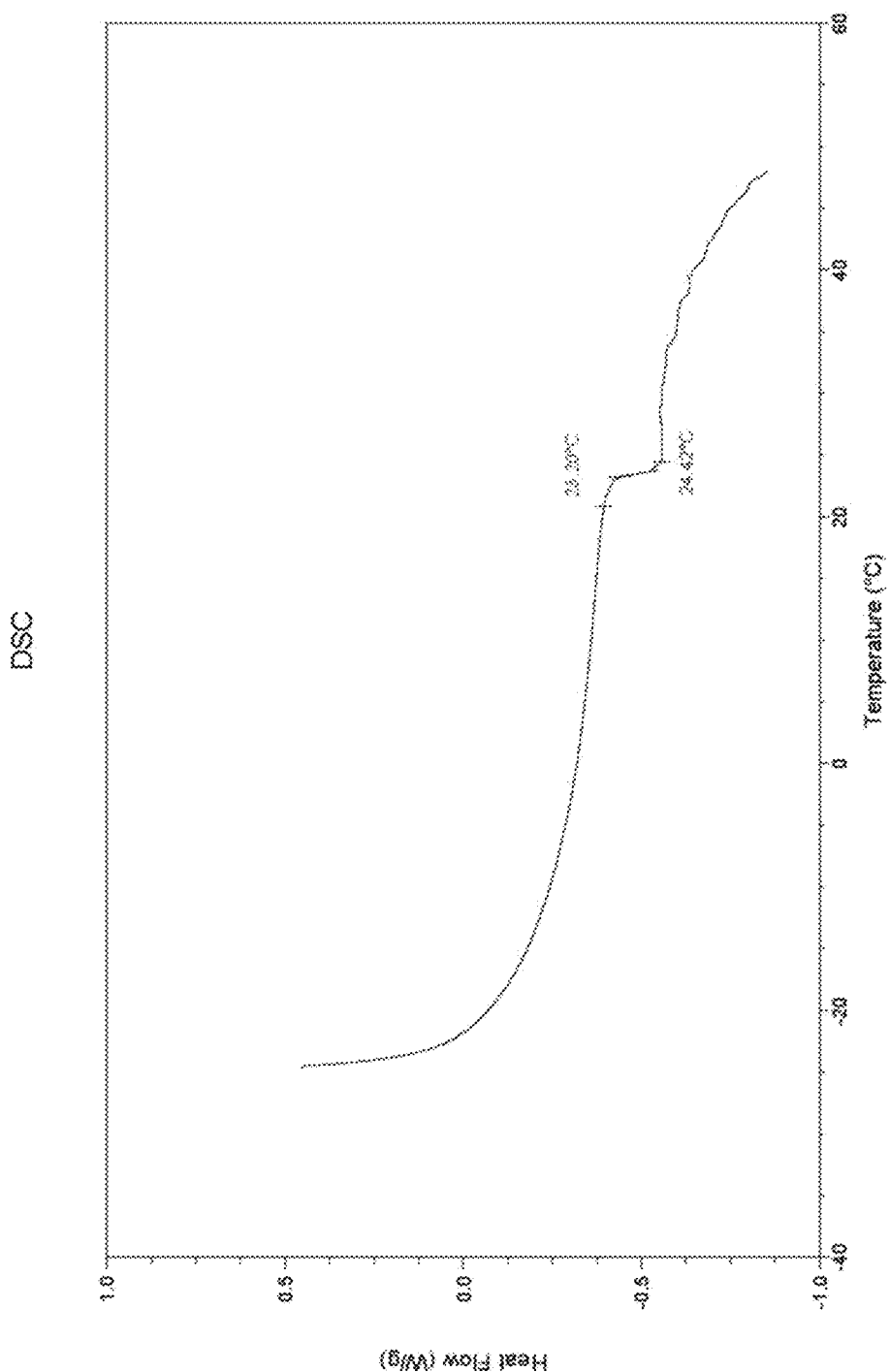
FIG. 3 shows the differential scanning calorimetry (DSC) analysis for a triethylamine plus 2-butanone in water solution demonstrating a change of enthalpy at 24.42° C., which coincides with the observed solubility/polarity shift.

In a second example, the inventor took equal molar ratios of 2-butanone as the enolisable carbonyl plus triethylamine as the base in a volume of water in a test tube. A DSC scan of that solution showed that there was a thermo-responsive point at 24.42° C. at which the lower critical solution temperature was reached—see FIG. 3. It was observed that close to that point the solution went from a miscible mixture of 2-butanone/tertiary amine in water to an immiscible mixture of 2-butanone/tertiary amine in water. A series of photographs shown as FIGS. 4A-C show the observable changes to the solution mixture. It can be seen in FIG. 4A at 26.65° C. the base and 2-butanone mixture is miscible. At 26.89° C. the base and ketone mixture has become turbid in appearance (see FIG. 4B) as a result of the base and ketone becoming an emulsion with the water. With a further temperature increase it can be seen in FIG. 4C that at 27.05° C. the base and 2-butanone are immiscible with the water.

The inventor has determined that the effect observed in the solutions is reproducible. The DSC analysis further determined that the solubility/polarity shift is an endothermic phenomenon, suggesting that some form of enthalpy of fusion is occurring and that the mixing of the components in their soluble state with water is exothermic. It is to be recognised that the different temperature at which the solubility/polarity switch is seen varies depending on the nature of the composition of the thermo-responsive solution. It is to be appreciated that over the temperature at which the solubility or polarity switch is seen the ketone base mixture passes from a miscible mixture through an emulsion to a ketone and base mixture that is immiscible with water.

Example 3

Figure 5A:
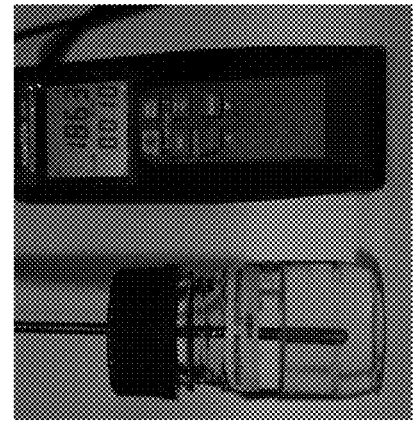
FIG. 5A-5C shows a series of photos showing the observable differences of a triethylamine plus cyclohexanone in water solution demonstrating a change in physical properties of the solution over a temperature range.
Figure 5B:
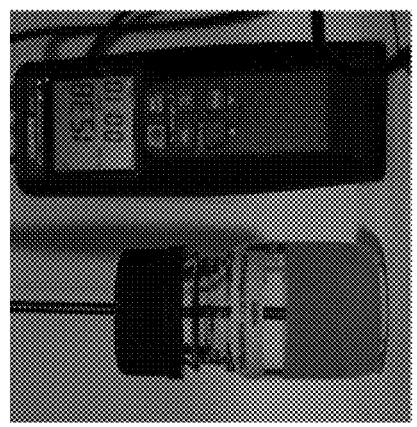
Figure 5C:

In a third example, the inventor took equal molar ratios of cyclohexanone as the enolisable carbonyl plus triethylamine as the base in a volume of water in a test vials and slowly increased the temperature of the mixture. A series of photographs shown as FIGS. 5A-5C show the observable changes to the solution mixture. The series of photographs show the observable differences of a triethylamine plus cyclohexanone in water solution demonstrating a change in physical properties of the solution over a temperature range. It can be seen in FIG. 5A at 15.21° C. the base and ketone mixture is miscible with water. At 15.38° C. the base and ketone mixture has become turbid in appearance (see FIG. 5B) as a result of the base and ketone becoming an emulsion with water and at 18.33° C. the base and ketone are immiscible with water (see FIG. 5C).

Example 4

It is to be understood that the LCST measured above in Examples 1 to 3 was supported by visual changes in terms of visibility or otherwise of the immiscible vs miscible layers. The exact point of the optical change can be difficult to judge visually. It has been found that it is easier to measure the optical properties of various test solutions to determine the transition of the LCST using a UV-Vis-NIR spectrometer. Transmittance of the test solutions at different temperatures was recorded using Stellar Net's SILVER-Nova fiber optic spectrometer which has a wide wavelength range of 190-1110 nm. The light source was SL1 tungsten-halogen lamps effective for reflectance, transmittance and absorbance measurements. A dip probe connected the light source and a spectrometer was used to measure the characteristics of the draw solution.

Materials and Methodology

Various test draw solutions were prepared using triethylamine (TEA), methyl ethyl ketone (MEK), N-ethylpiperidine, diethylmethylamine, cyclohexanone and diethylmethylamine and water various molar ratios and combinations in a 25 mL glass vial. The transmittance was recorded for every 2 seconds at a wavelength of 850 nm over varying temperatures. Resistance temperature detector (RTD) probe was inserted along with the dip probe to record the temperatures simultaneous to the episodes captured every 2 seconds. The main objective was to record a transition in the transmittance at the LCST where the solution transforms from a clear solution (100% transmittance) below LCST to cloudy above it. The controller used to ramp the temperature at the rate of 2° C./min was a Qpod-2e which has Peltier based cuvette holder with magnetic stirring. For one test solution using TEA, MEK and water in the molar ratios of 0.5:1:5 (respectively) first and second derivative curves were also obtained.

Results

Figure 6:
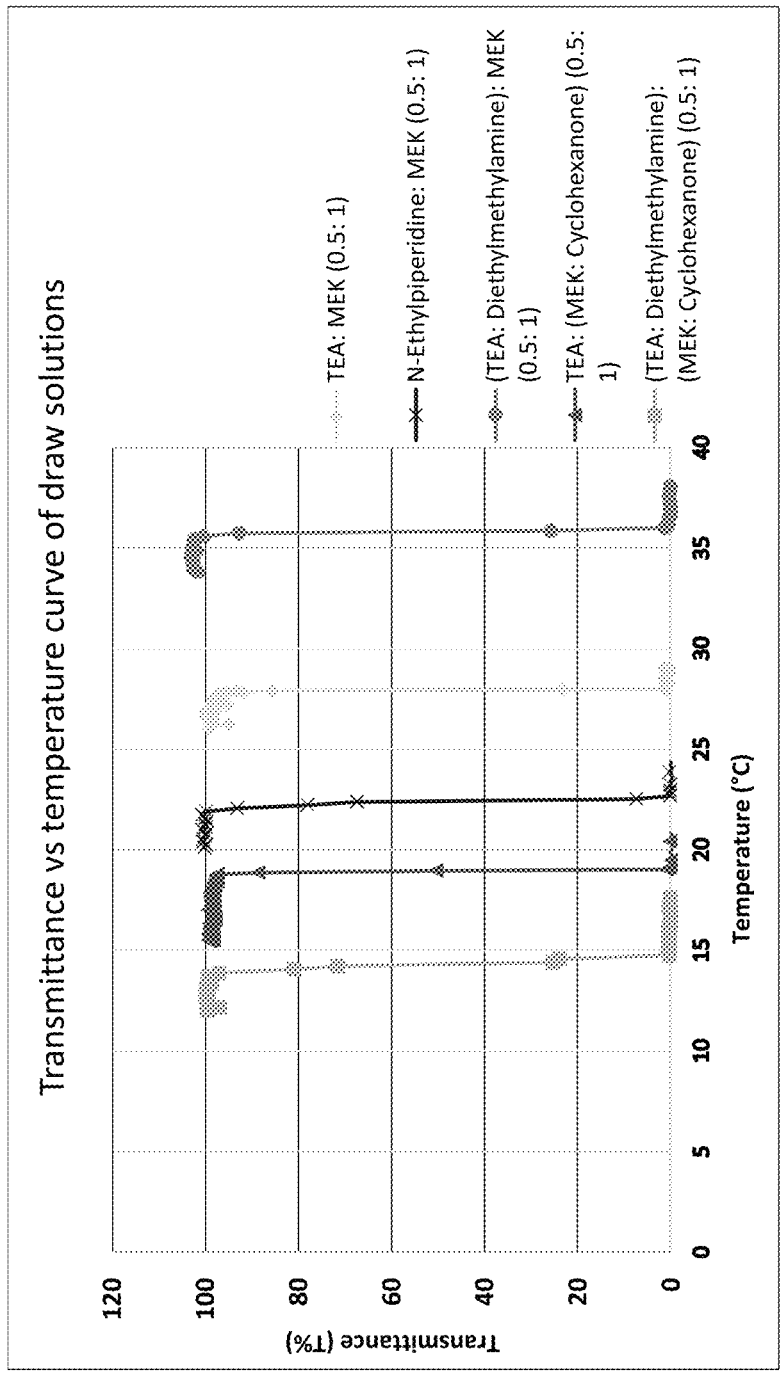
FIG. 6 shows the transmittance versus temperature plots of various draw solutions showing a clear change in transmission at the LCST of the respective draw solution.

Data from the experiment was used to obtain the transmittance % vs temperature curves at 850 nm as shown in FIG. 6. FIG. 6 shows the transmittance curve of the draw solutions recorded at varying temperatures at 850 nm. A sharp drop in transmission % was observed for all draw solutions at the LCST. For one test solution using TEA, MEK and water in the molar ratios of 0.5:1:5 (respectively) a transmission curve was obtained as shown in FIG. 7A and then first and second derivative curves as shown in FIG. 7B and FIG. 7C, respectively, were also obtained. The inventors are of the view that the point at which the curve intersects the x-axis at just under 28 degrees C. of the second derivative curve is to be taken as the LCST for that particular test solution.

Example 5: Molar Ratio

In a fourth example, the molar ratios of various thermo-responsive solutions comprising triethylamine and a ketone in water at different temperatures were measured and the miscibility of the solution in water was recorded. The results are tabulated below in Table 1-4.

TABLE 1

| | | Components | | |
|---|---|---|---|---|
| Mol Ratio | water 144:0 | water; triethylamine; propanone 144:6:6 | water; triethylamine; 2-butanone 144:6:6 | water; triethylamine; cyclohexanone 144:6:6 |
| 5° C. | miscible | miscible | miscible | miscible |
| 20° C. | miscible | miscible | miscible | immiscible |
| 50° C. | miscible | immiscible | immiscible | immiscible |

Table 2 shows a table of a range of molar ratios of trimethylamine to 2-butanone in 500 μL of water and the observed effect on the aqueous phase at 5° C. and 50° C.

TABLE 2

| Mol Ratio triethylamine:2-butanone | | triethylamine (mol · L⁻¹) | 2-butanone (mol · L⁻¹) | Water (uL) | triethylamine (uL) | 2-butanone (uL) | Aqueous Phase (observed) | |
|---|---|---|---|---|---|---|---|---|
| | | | | | | | 5° C. ** | 50° C. ** |
| 1 | 99 | 0.059 | 5.797 | 500.0 | 8.17 | 491.83 | clear | turbid |
| 2 | 98 | 0.116 | 5.702 | 500.0 | 16.23 | 483.77 | clear | turbid |
| 3 | 97 | 0.173 | 5.609 | 500.0 | 24.19 | 475.81 | clear | turbid |
| 4 | 96 | 0.230 | 5.516 | 500.0 | 32.06 | 467.94 | clear | turbid |
| 5 | 95 | 0.285 | 5.424 | 500.0 | 39.82 | 460.18 | clear | turbid |
| 10 | 90 | 0.554 | 4.983 | 500.0 | 77.23 | 422.77 | clear | turbid |
| 20 | 80 | 1.044 | 4.177 | 500.0 | 145.65 | 354.35 | clear | turbid |
| 30 | 70 | 1.482 | 3.458 | 500.0 | 206.68 | 293.32 | clear | turbid |
| 40 | 60 | 1.875 | 2.812 | 500.0 | 261.46 | 238.54 | clear | turbid |
| 50 | 50 | 2.229 | 2.229 | 500.0 | 310.90 | 189.10 | clear | turbid |
| 60 | 40 | 2.551 | 1.700 | 500.0 | 355.75 | 144.25 | clear | turbid |
| 70 | 30 | 2.844 | 1.219 | 500.0 | 396.61 | 103.39 | clear | turbid |
| 80 | 20 | 3.112 | 0.778 | 500.0 | 434.00 | 66.00 | clear | turbid |
| 90 | 10 | 3.358 | 0.373 | 500.0 | 468.35 | 31.65 | clear | turbid |
| 95 | 5 | 3.474 | 0.183 | 500.0 | 484.49 | 15.51 | clear | turbid |
| 96 | 4 | 3.496 | 0.146 | 500.0 | 487.64 | 12.36 | clear | turbid |
| 97 | 3 | 3.519 | 0.109 | 500.0 | 490.77 | 9.23 | clear | turbid |

TABLE 2-continued

| Mol Ratio triethylamine:2-butanone | triethylamine (mol·L⁻¹) | 2-butanone (mol·L⁻¹) | Water (uL) | triethylamine (uL) | 2-butanone (uL) | Aqueous Phase (observed) 5° C. ** | 50° C. ** |
|---|---|---|---|---|---|---|---|
| 98 | 2 | 3.541 | 0.072 | 500.0 | 493.87 | 6.13 | clear | turbid |
| 99 | 1 | 3.563 | 0.036 | 500.0 | 496.95 | 3.05 | clear | turbid |

** stablisation at 5° C. for 30 mins, immersion in 50° C. for 10 seconds, observe Table 3 shows a table of a range of molar ratios of trimethylamine to propanone in 500 μL of water and the observed effect on the aqueous phase at 5° C. and 50° C.

TABLE 3

| Mol Ratio triethylamine:propanone | triethylamine (mol·L⁻¹) | propanone (mol·L⁻¹) | Water (uL) | triethylamine (uL) | propanone (uL) | Aqueous Phase (observed) 5° C. ** | 50° C. ** |
|---|---|---|---|---|---|---|---|
| 1 | 99 | 0.061 | 6.084 | 500.0 | 8.57 | 491.43 | clear | turbid |
| 2 | 98 | 0.122 | 5.979 | 500.0 | 17.02 | 482.98 | clear | turbid |
| 3 | 97 | 0.182 | 5.876 | 500.0 | 25.35 | 474.65 | clear | turbid |
| 4 | 96 | 0.241 | 5.774 | 500.0 | 33.56 | 466.44 | clear | turbid |
| 5 | 95 | 0.299 | 5.674 | 500.0 | 41.65 | 458.35 | clear | turbid |
| 10 | 90 | 0.577 | 5.193 | 500.0 | 80.48 | 419.52 | clear | turbid |
| 20 | 80 | 1.081 | 4.323 | 500.0 | 150.76 | 349.24 | clear | turbid |
| 30 | 70 | 1.525 | 3.557 | 500.0 | 212.64 | 287.36 | clear | turbid |
| 40 | 60 | 1.918 | 2.877 | 500.0 | 267.56 | 232.44 | clear | turbid |
| 50 | 50 | 2.270 | 2.270 | 500.0 | 316.62 | 183.38 | clear | turbid |
| 60 | 40 | 2.586 | 1.724 | 500.0 | 360.72 | 139.28 | clear | turbid |
| 70 | 30 | 2.872 | 1.231 | 500.0 | 400.57 | 99.43 | clear | turbid |
| 80 | 20 | 3.131 | 0.783 | 500.0 | 436.76 | 63.24 | clear | turbid |
| 90 | 10 | 3.368 | 0.374 | 500.0 | 469.77 | 30.23 | clear | turbid |
| 95 | 5 | 3.479 | 0.183 | 500.0 | 485.21 | 14.79 | clear | turbid |
| 96 | 4 | 3.500 | 0.146 | 500.0 | 488.22 | 11.78 | clear | turbid |
| 97 | 3 | 3.522 | 0.109 | 500.0 | 491.20 | 8.80 | clear | turbid |
| 98 | 2 | 3.543 | 0.072 | 500.0 | 494.16 | 5.84 | clear | turbid |
| 99 | 1 | 3.564 | 0.036 | 500.0 | 497.09 | 2.91 | clear | turbid |

** stablisation at 5° C. for 30 mins, immersion in 50° C. for 10 seconds, observe Table 4 shows a table of a range of molar ratios of trimethylamine to cyclohexanone in 500 μL of water and the observed effect on the aqueous phase at 5° C. and 50° C.

TABLE 4

| Mol Ratio triethylamine:cyclohexanone | Triethylamine (mol·L⁻¹) | cyclohexanone (mol·L⁻¹) | Water (uL) | triethylamine (uL) | cyclohexanone (uL) | Aqueous Phase (observed) 5° C. ** | 50° C. ** |
|---|---|---|---|---|---|---|---|
| 1 | 99 | 0.048 | 4.764 | 500.0 | 6.71 | 493.29 | clear | turbid |
| 2 | 98 | 0.096 | 4.699 | 500.0 | 13.38 | 486.62 | clear | turbid |
| 3 | 97 | 0.143 | 4.635 | 500.0 | 20.00 | 480.00 | clear | turbid |
| 4 | 96 | 0.190 | 4.572 | 500.0 | 26.57 | 473.43 | clear | turbid |
| 5 | 95 | 0.237 | 4.509 | 500.0 | 33.10 | 466.90 | clear | turbid |
| 10 | 90 | 0.467 | 4.200 | 500.0 | 65.09 | 434.91 | clear | turbid |
| 20 | 80 | 0.903 | 3.612 | 500.0 | 125.95 | 374.05 | clear | turbid |
| 30 | 70 | 1.312 | 3.061 | 500.0 | 182.99 | 317.01 | clear | turbid |
| 40 | 60 | 1.696 | 2.544 | 500.0 | 236.55 | 263.45 | clear | turbid |
| 50 | 50 | 2.057 | 2.057 | 500.0 | 286.95 | 213.05 | clear | turbid |
| 60 | 40 | 2.398 | 1.599 | 500.0 | 334.45 | 165.55 | clear | turbid |
| 70 | 30 | 2.720 | 1.166 | 500.0 | 379.31 | 120.69 | clear | turbid |
| 80 | 20 | 3.024 | 0.756 | 500.0 | 421.72 | 78.28 | clear | turbid |
| 90 | 10 | 3.312 | 0.368 | 500.0 | 461.90 | 38.10 | clear | turbid |
| 95 | 5 | 3.450 | 0.182 | 500.0 | 481.20 | 18.80 | clear | turbid |
| 96 | 4 | 3.477 | 0.145 | 500.0 | 485.00 | 15.00 | clear | turbid |
| 97 | 3 | 3.504 | 0.108 | 500.0 | 488.78 | 11.22 | clear | turbid |
| 98 | 2 | 3.531 | 0.072 | 500.0 | 492.54 | 7.46 | clear | turbid |
| 99 | 1 | 3.558 | 0.036 | 500.0 | 496.28 | 3.72 | clear | turbid |

** stablisation at 5° C. for 30 mins, immersion in 50° C. for 10 seconds, observe Example 6—Ketone and Amine Combinations In a fifth example, the molar ratios of various thermo-responsive solutions comprising triethylamine and a mixture of ketones in water at different temperatures were measured and the miscibility of the solution in water was recorded. The results are tabulated below in Table 5.

TABLE 5

| | Components | | | |
|---|---|---|---|---|
| Mol Ratio | water; triethylamine; propanone; 2-butanone 144:6:3:3 | water; triethylamine; propanone; cyclohexanone 144:6:3:3 | water; triethylamine; 2-butanone; cyclohexanone 144:6:3:3 | water; triethylamine; propanone; 2-butanone; cyclohexanone 144:6:2:2:2 |
| 5° C. | miscible | miscible | miscible | miscible |
| 20° C. | miscible | miscible | immiscible | miscible |
| 50° C. | immiscible | immiscible | immiscible | immiscible |

It can be seen from the tabulated results that combinations of ketone mixtures are equally as effective as a single ketone. It can also be noted that the temperatures at which immiscibility occurs can be controlled by selection of the components of the ketone mixture.

Minimum Ratios of Amine, Ketones and Water

The following experiments were carried out to determine the minimum ratio of amine, ketone and water respectively in the draw solution to behave as a switchable polar draw solution. The major objective of this experiment was to learn how to manage the solution components in the most economical manner. The model draw solution used for this test was a combination of triethylamine (TEA), methyl ethyl ketone (MEK) and water.

Minimum Molar Ratio of Amine

The draw solution was prepared using TEA, MEK and water with the molar ratio of TEA varying from 0.1 to 1 in 25 mL glass vials. The quantity and number of moles of TEA with respect to the molar ratio was tabulated (as shown in Table 6). A constant molar ratio of 1:10 for MEK (4.0061 g) and water (10 g) was maintained throughout. For all the test samples, the visual LCST was recorded using a resistance temperature detector (RTD).

TABLE 6

Visual LCST data of the draw solution containing TEA, MEK and water with varying ratios of TEA

| | Triethylamine (TEA) | | |
|---|---|---|---|
| Quantity | Number of moles | Molar ratio | LCST (in ° C.) |
| 0.5621 | 0.0050 | 0.1 | 23.7-24.3 |
| 1.1243 | 0.0100 | 0.2 | 24.2-24.5 |
| 1.68655 | 0.0150 | 0.3 | 26.6-26.8 |
| 2.2487 | 0.0200 | 0.4 | 27.3-27.5 |
| 2.8109 | 0.0250 | 0.5 | 27.6-27.7 |
| 3.3731 | 0.0300 | 0.6 | 27.6-27.8 |
| 3.93528 | 0.0350 | 0.7 | 27.6-27.8 |
| 4.497467 | 0.0400 | 0.8 | 27.2-27.4 |
| 5.05965 | 0.0450 | 0.9 | 27.2-27.5 |
| 5.6218 | 0.0500 | 1 | 27.5-27.8 |

From FIG. 8, it can be seen that the LCST increased with an increase in the molar ratio of TEA from 0.1 to 0.4 in the draw solution. For the molar ratios greater than 0.4, the LCST remained the same. From these results the minimum molar ratio of TEA required is 0.5 for the draw solution to behave as a switchable polar solution without altering the LCST.

Minimum Molar Ratio of Ketone

The draw solution was prepared by using TEA, MEK and water with the molar ratio of MEK varying from 0.1 to 1 in 25 mL glass vials. The quantity and number of moles of MEK with respect to the molar ratio was tabulated (as shown in Table 7). A constant molar ratio of 1:10 for TEA (5.6218 g) and water (10 g) was maintained throughout. For all the samples, the visual LCST was recorded using a resistance temperature detector (RTD).

TABLE 7

Visual LCST data of the draw solution containing TEA, MEK and water with varying ratios of MEK.

| | MEK | | LCST |
|---|---|---|---|
| Ratio | Quantity(g) | Moles | (in ° C.) |
| 0.1 | 0.4006 | 0.0050 | 19.6-19.8 |
| 0.2 | 0.8012 | 0.0100 | 21.2-21.3 |
| 0.3 | 1.2018 | 0.0150 | 22.4-22.6 |
| 0.4 | 1.6024 | 0.0200 | 23.7-23.8 |
| 0.5 | 2.0031 | 0.0250 | 24.5-24.7 |
| 0.6 | 2.4037 | 0.0300 | 25.3-25.6 |
| 0.7 | 2.8043 | 0.0350 | 25.9-26.02 |
| 0.8 | 3.2049 | 0.0400 | 26.4 |
| 0.9 | 3.6055 | 0.0450 | 27.1 |

From FIG. 9, it can be seen that the visual LCST values are increasing with an increase in the molar ratios of MEK and there is no point at which it stabilises or becomes constant. Thus, for all the draw solution formulations, the molar ratio of ketone is maintained as 1.

Example 7—Volume Ratios

In a sixth example, the volumetric ratios of the various components of a thermo-responsive solutions in water at 20 degrees C. were studied and their respective miscibilities in water were recorded. The results are tabulated below in Table 8.

TABLE 8

| Vol Ratio | water 50:50 | water; propanone 50:50 | water; 2-butanone 50:50 | water; cyclohexanone 50:50 | water; triethylamine 50:50 |
|---|---|---|---|---|---|
| 20° C. | miscible | miscible | immiscible | immiscible | immiscible |

Example 8—Controls

In a seventh example, the various components of a thermo-responsive solutions in water at 20, 30 and 50 degrees C. were studied and their respective miscibilities in water were recorded. The results are tabulated below in Tables 9 and 10.

TABLE 9

| | water | water; triethylamine | water; 2-butanone | water; triethylamine; 2-butanone | triethylamine; 2-butanone |
|---|---|---|---|---|---|
| 20° C. | miscible | immiscible | immiscible | miscible | miscible |
| 30° C. | miscible | immiscible | immiscible | immiscible | miscible |
| 50° C. | miscible | immiscible | immiscible | immiscible | miscible |

TABLE 10

| | water | water; triethylamine | water; propanone | water; triethylamine; propanone | triethylamine; propanone |
|---|---|---|---|---|---|
| 20° C. | miscible | immiscible | miscible | miscible | miscible |
| 30° C. | miscible | immiscible | miscible | miscible | miscible |
| 50° C. | miscible | immiscible | miscible | immiscible | miscible |

It can be seen from Tables 9 and 10 that the miscibility properties of the components can vary significantly depending on the temperature and the components in the mixture. For example, it can be seen in Table 4 that at 20 degrees Celsius (C), both triethylamine and 2-butanone are immiscible in water. However, at the same temperature, a mixture of both triethylamine and 2-butanone in water is miscible, while at 30 degrees C. the mixture becomes immiscible. This exemplifies a thermo-responsive solution.

Similar results are seen in Table 10, with the exception that in this example, the ketone, propanone, is miscible in water, whereas in contrast in Table 9, 2-butanone was immiscible in water.

Multiple Amines and Single Ketone

The compounds being used to prepare switchable polar draw solutions for various applications are bases and enolisable carbonyls. Tertiary amines which are basic in nature are combined with ketones which are organic compounds with a carbonyl group and the resulting combinations are checked for a lower critical solution temperature (LCST). The effect of conjugation, substitution and addition of functional groups on the switch point are observed and the data obtained are put to further use depending on the applications in the future. Ketones are selected such that they are in series (for example, 2-propanone, 2-butanone and so on), isomers (for example, 2-pentanone and 3-pentanone), cyclic (for example, cyclopentanone) and conjugated (for example, acetophenone) in nature.

The draw solutions were formulated to consist of multiple amines and ketones whilst still exhibiting thermo-responsive properties. The ketones were combined with few selected amines in different molar ratios and the LCSTs were recorded on addition of water. Several combinations are described in the following experiment. Additionally, the effect of different ketone/amine combinations on the osmotic pressure was observed.

Instruments

The temperature was varied to determine the LCST using Qpod-2e which is a Peltier based cuvette holder with constant stirring. The visual LCST temperature was recorded using resistance temperature detector (RTD) probe. The osmolality of the draw solution at 10% by weight in water was determined by freezing point method based osmometer, Osmomat 3000.

Methodology

The draw solutions were made up with amine(s), ketone(s) and water in the specified molar ratios and the visual LCST of the draw solution was determined. Visual LCST refers to the temperature at which the solution turns cloudy just before it separates out into two phases and the LCST was recorded using the resistance temperature detector (RTD) probe.

Osmotic pressure of the draw solution was measured for the draw solution with 10% pure draw (by weight) in 90% water (by weight). 50 μL of the test sample (chilled draw solution in single phase) was pipetted out into the measuring vessel and attached to the thermistor probe of the osmometer. The test draw solution sample measurement was performed automatically and the osmolality of solute (pure draw) was displayed on the screen. At least 3 trials were performed on each sample and the average was reported.

Types of Combinations

Different types of amines and ketones were combined in different combinations such that they would behave as a switchable polar draw solution. A few draw solution combinations were selected as follows:
  Single amine combined with ketone(s)
  Multiple amines combined with single ketone
  Multiple amines combined with multiple ketones
The following abbreviations are used in Tables 11-14:
K1=Ketone 1, K2=Ketone 2, K3=Ketone 3; A1=Amine 1, A2=Amine 2, A3=Amine 3, TEA=triethylamine, 2-P=2-propanone, 2-PENT=2-pentanone, 3-P=3-pentanone, 2-B=2-Butanone, CH=cyclohexanone, CP=cyclopentanone, 1EP=1 ethylpiperidine, DEMA=diethylmethylamine, ACET=acetophenone, 2-O=2-octanone, 4M2P=4-Methyl-2-pentanone, 3M2B=3-methyl-2-butanone, DMBA=dimethylbenzylamine.

The following Table 11 summarises the LCST and the osmotic pressure of different combinations of draw solutions containing a single amine with one or more ketone(s): Note: the osmotic pressure is at 10% of pure draw by weight.

TABLE 11

| A1 | K1 | K2 | K3 | Molar ratio of amine:ketone:water | Visual LCST (° C.) | Osmotic pressure (mOsmol/kg) |
|---|---|---|---|---|---|---|
| TEA | 2-P | — | — | 6:6:144 | 45 | 923.67 |
| TEA | 2-B | — | — | 6:6:144 | 27 | 1350 |
| TEA | CH | — | — | 6:6:144 | 11.5 | 905.33 |
| TEA | 2-B | 2-P | — | 6:3:3:144 | 28.3 | 1251.000 |
| TEA | 2-P | CH | — | 6:3:3:144 | 22.8 | 710.000 |
| TEA | 2-B | CH | — | 6:3:3:144 | 20.5 | 1020.333 |
| TEA | 2-P | 2-B | CH | 6:2:2:2:144 | 25.3 | 1097.333 |

Combination of Multiple Amines and Single Ketone

The following table 12 summarises the LCST and the osmotic pressure of combinations of draw solutions containing multiple amines with a single ketone: Note: the osmotic pressure is measured at 10% of pure draw by weight.

TABLE 12

| A1 | A2 | A3 | K1 | Molar ratio amines:ketone:water | Visual LCST (° C.) | Osmotic pressure (mOsmol/kg) |
|---|---|---|---|---|---|---|
| TEA | 1-EP | — | 2-B | 0.5:1:10 | 22.7 | 1114 |
| TEA | DEMA | — | 2-B | 0.5:1:10 | 35.8 | 1150.3 |
| TEA | 1-EP | DEMA | 2-B | 0.5:1:10 | 31.3 | 1258.3 |
| TEA | 1-EP | — | CP | 0.5:1:10 | 22.7 | 1098.67 |
| TEA | DEMA | — | CP | 0.5:1:10 | 32 | 1054 |
| TEA | 1-EP | DEMA | CP | 0.5:1:10 | 41.6 | 1180.3 |

Combination of Amine(s) and Two Ketones

The following table 13 summarises the LCST and the osmotic pressure of combinations of draw solutions containing one or more amine(s) with two ketones: Note: the Osmotic pressure is at 10% of pure draw by weight.

TABLE 13

| A1 | A2 | K1 | K2 | Molar ratio amine(s):ketone(s):water | Visual LCST (° C.) | Osmotic pressure (mOsmol/kg) |
|---|---|---|---|---|---|---|
| TEA | — | 2-P | 2-PENT | 0.5:1:10 | 35.7 | 1323.3 |
| 1-EP | — | 2-P | 2-PENT | 0.5:1:10 | 22.5 | 1284.3 |
| TEA | 1-EP | 2-P | 2-PENT | 0.5:1:10 | 31.9 | 1181 |
| TEA | — | CP | ACET | 0.5:1:10 | 15.6 | 1017 |
| 1-EP | — | CP | ACET | 0.5:1:10 | 6.5 | 995 |
| TEA | 1-EP | CP | ACET | 0.5:1:10 | 10.5 | 993.67 |
| TEA | — | CP | 2-O | 0.5:1:10 | 6.7 | 1006.6 |
| 1-EP | — | CP | 2-O | 0.5:1:10 | 0 | 840.6 |
| TEA | 1-EP | CP | 2-O | 0.5:1:10 | 1.5 | 868 |
| TEA | — | CP | 4M2P | 0.5:1:10 | 13.1 | 1141 |
| 1-EP | — | CP | 4M2P | 0.5:1:10 | 9.5 | 1013.3 |
| TEA | 1-EP | CP | 4M2P | 0.5:1:10 | 12.3 | 1059.3 |

Combination of Amine(s) and Multiple Ketones

The following table 14 summarises the LCST and the osmotic pressure of draw solutions containing combination of one or more amine(s) with multiple ketones:

TABLE 14

| A1 | A2 | A3 | K1 | K2 | K3 | Molar ratio of A(s):K(s):water | Visual LCST (° C.) | Osmotic pressure at 10% of pure draw by weight (mOsmol/kg) |
|---|---|---|---|---|---|---|---|---|
| TEA | — | — | 2-B | CP | 2-P | 0.5:1:10 | 30.5 | 1096.33 |
| 1-EP | — | — | 2-B | CP | 2-P | 0.5:1:10 | 29.3 | 1172.67 |
| TEA | 1-EP | DMBA | 2-B | CP | 2-P | 0.5:1:10 | 24 | 993.67 |
| TEA | — | — | 2-P | 3-P | 3M2B | 0.5:1:10 | 15.2 | 1107 |
| 1-EP | — | — | 2-P | 3-P | 3M2B | 0.5:1:10 | 5.6 | 972 |
| TEA | 1-EP | DMBA | 2-P | 3-P | 3M2B | 0.5:1:10 | −1 | 983 |

From these results it can be appreciated that effective LCST draw solutions can be prepared from a number of amines and ketones in various combinations and ratios. The results also show that a very wide spread of different temperature LCST draw solutions can be obtained and that a desired temperature of a LCST draw solution could be achieved by using different amines and ketones. It is also to be appreciated that if the LCST of a given draw solution is too high or too low, the LCST could be modified by adding a ketone or an amine. It can also be seen from the results that significant osmotic pressure readings are obtained with a number of these draw solutions.

Example 9—Flux Experiment

Figure 10:
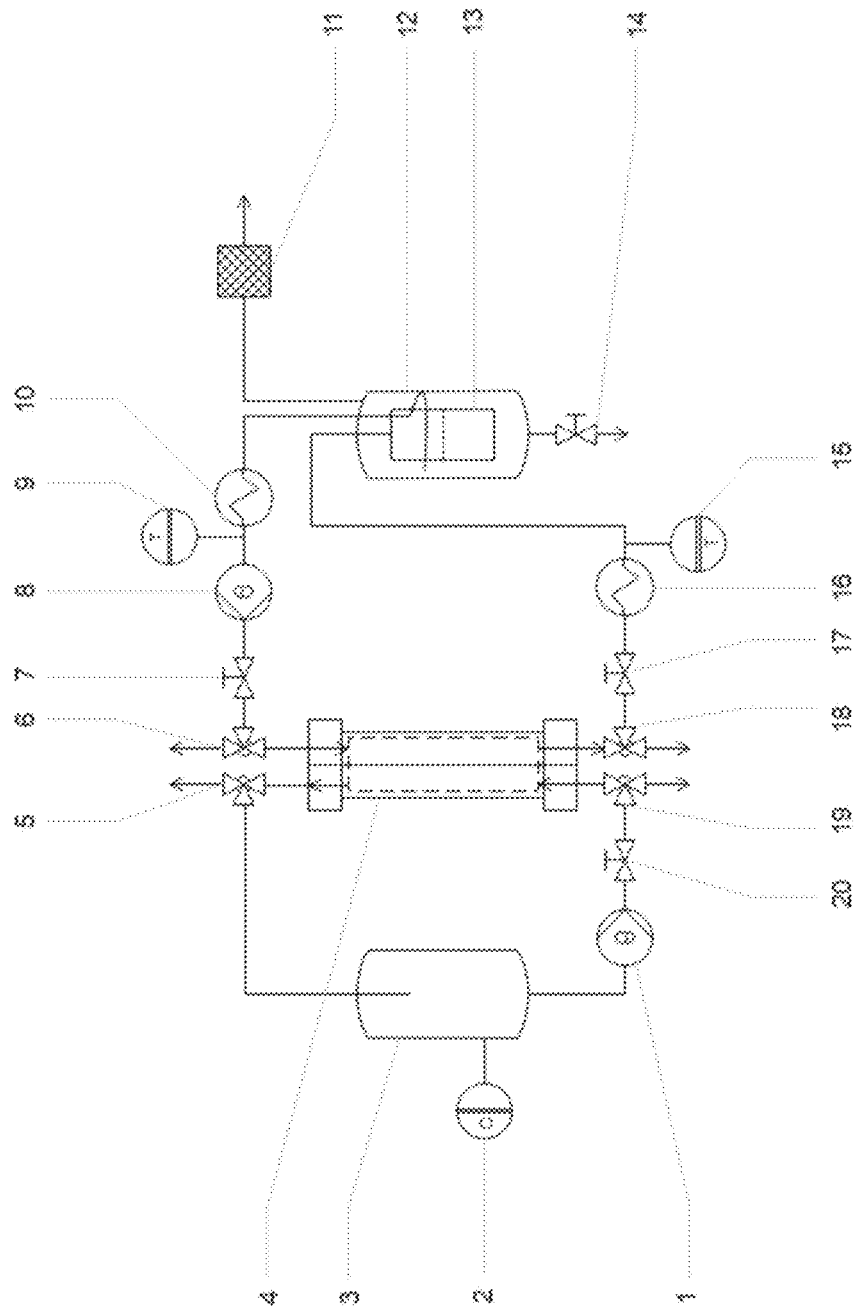
FIG. 10 shows schematically the flux experiment setup described below in the examples.

The flux of water across a semipermeable membrane using draw solutions of the present invention (as detailed in Table 15) have been studied using a test system as illustrated in FIG. 10. The test system comprises a gear pump (1) that is used to circulate the feed from the feed tank (3) into the membrane cell (4). A conductivity probe (2) is used to measure the conductivity in the feed tank (3). Three way valve (5) on the feed side of the membrane cell (4) and three way valve (6) on the draw side of the membrane cell (4) are used to isolate the membrane cell when cleaning or replacing the membrane. Another valve (7) is used to isolate the draw side when maintenance is required. This valve (7) can also be used then cleaning or replacing the membrane. A gear pump (8) on the draw side is used to circulate the draw solution into the membrane cell. A resistance temperature detector (9) is used to control the temperature after the chiller (10), which is a heat exchange used to coll the draw solution before entering the membrane cell (4). A filter (11) is shown that allows the flux experiment to be run at atmospheric pressure without exposing the operator to vapors or fumes. A coalescer cartridge (12) is used to collect the draw solution and water after the membrane cell (4). A draw tank and coalescer (13) are used for separation of the draw solution from water. At the bottom of the draw tank and coalescer (13) is a valve (1) that is used to drain the tank/coalescer. A resistance temperature detector (15) is used to control the temperature after the heater (16), which is a heat exchanger used to heat the draw solution before being returned to the draw tank and coalesce (13). Two way valve (17) is used to isolate the draw side when cleaning or replacing the membrane. Three way valve (18) on the draw side of the membrane cell (4) and three way valve (19) on the draw side of the membrane cell (4) are used to isolate the membrane cell when cleaning or replacing the membrane. Two way valve (20) is used to isolate the feed side when cleaning or replacing the membrane. The test system was flushed with deionised water (in triplicate) on each side of the semipermeable membrane in the membrance cell (4). The semipermeable membrane was a forward osmosis membrane. The feed side of the membrane cell was filled with deionised water and the draw side of the membrane cell was filled with the selected draw solution being tested. The feed solution pump (1) and draw solution pump (8) were then turned on simultaneously and the test system was left to equilibrate for 2-3 minutes. The water level in the draw tank (13) was recorded and then the system was allowed to operate for 10 minutes. The draw tank (13) was then emptied by removing the water down to the originally noted level in the draw tank and the water was weighed to determine the quantity of water that crossed that membrane in 10 minutes. These last two steps were repeated for the duration of the test. The ratios, draw concentrations and duration of the tests conducted are tabulated below in Table 15.

TABLE 15

Figure 11:
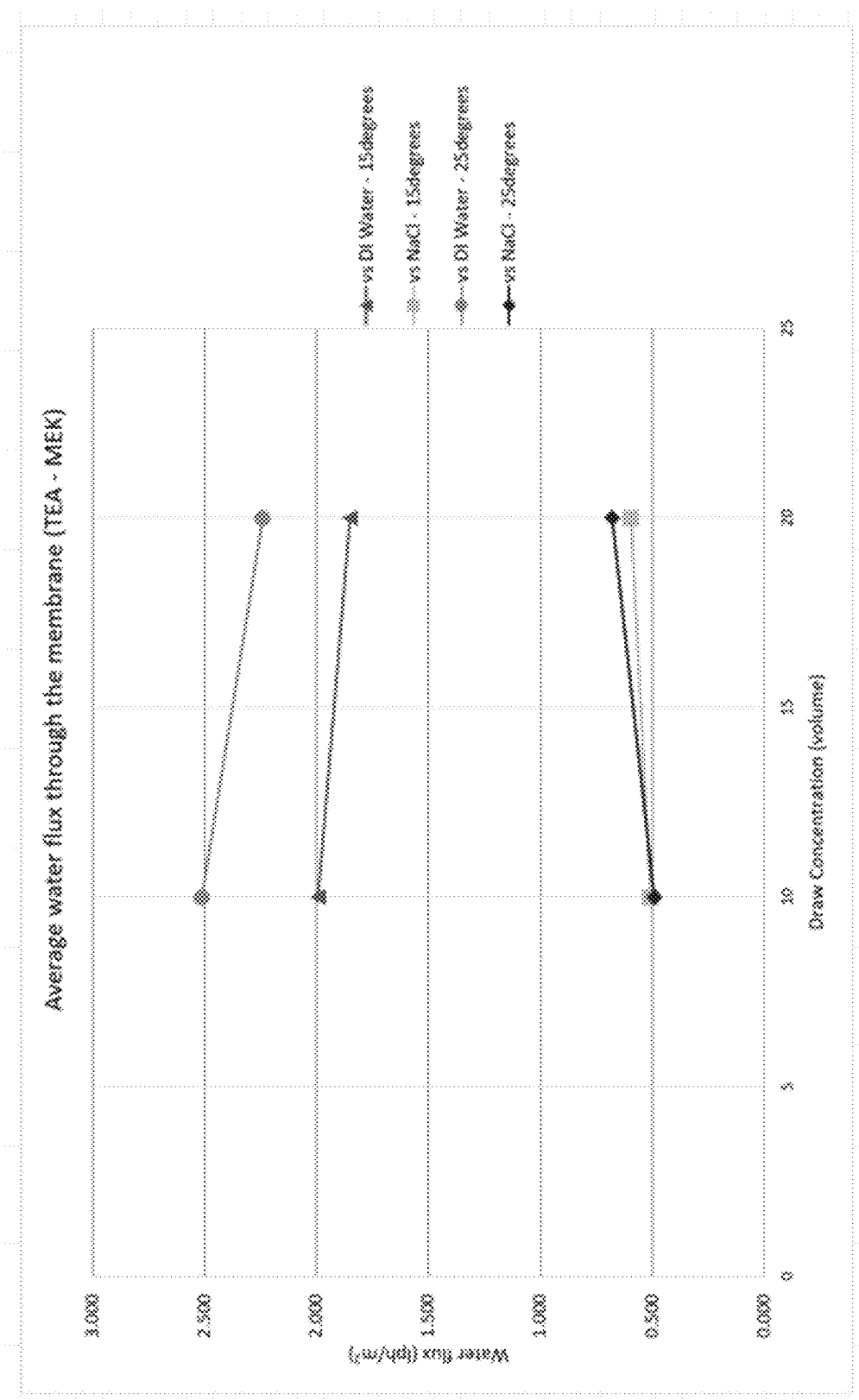
FIG. 11 shows a plot of the average water flux through a membrane involving a TEA-MEK draw solution.
Figure 12:
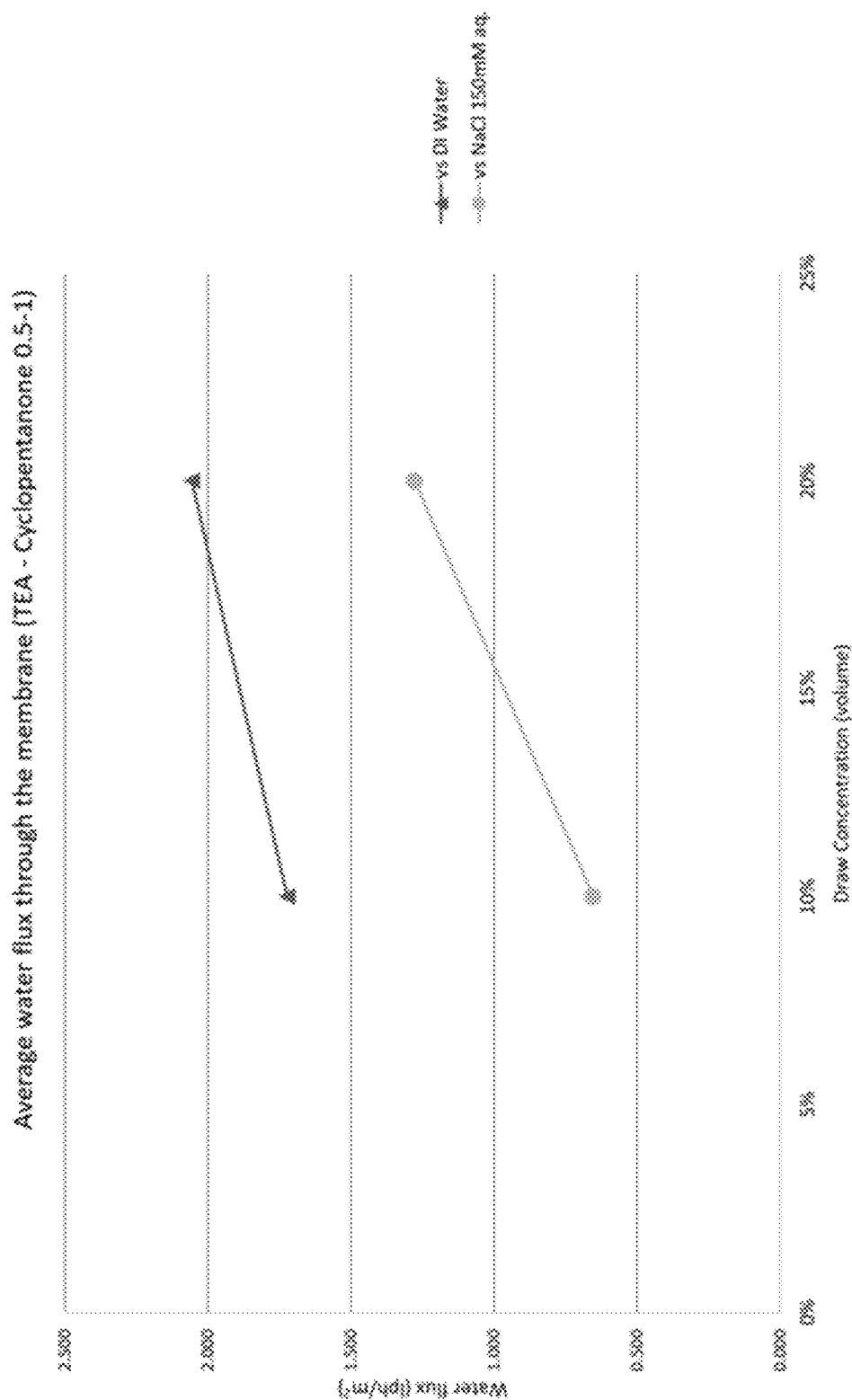
FIG. 12 shows a plot of the average water flux through a membrane involving a TEA-cycloppentanone draw solution.
Figure 13:
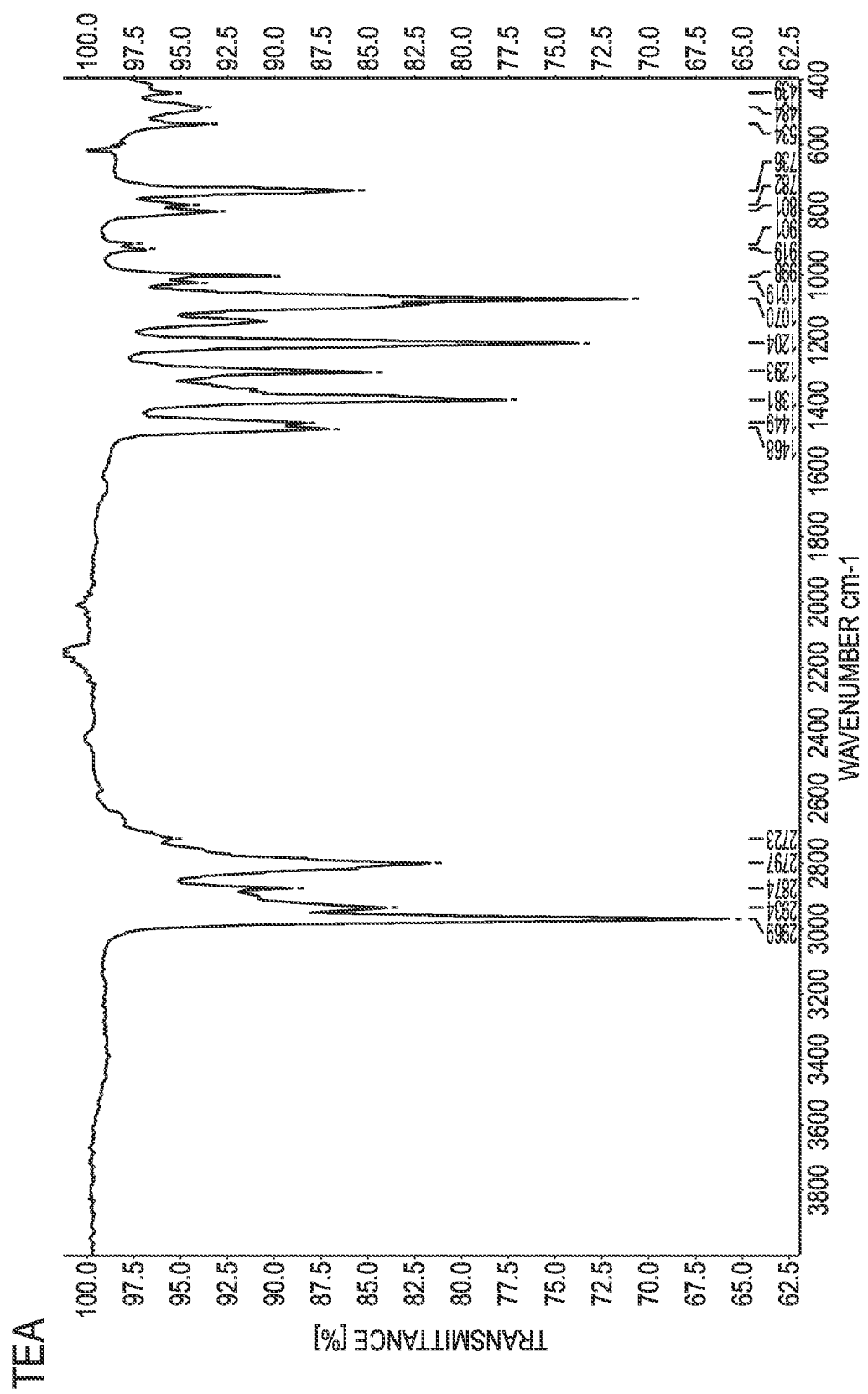
FIG. 13 shows the FTIR spectra of TEA.
Figure 14:
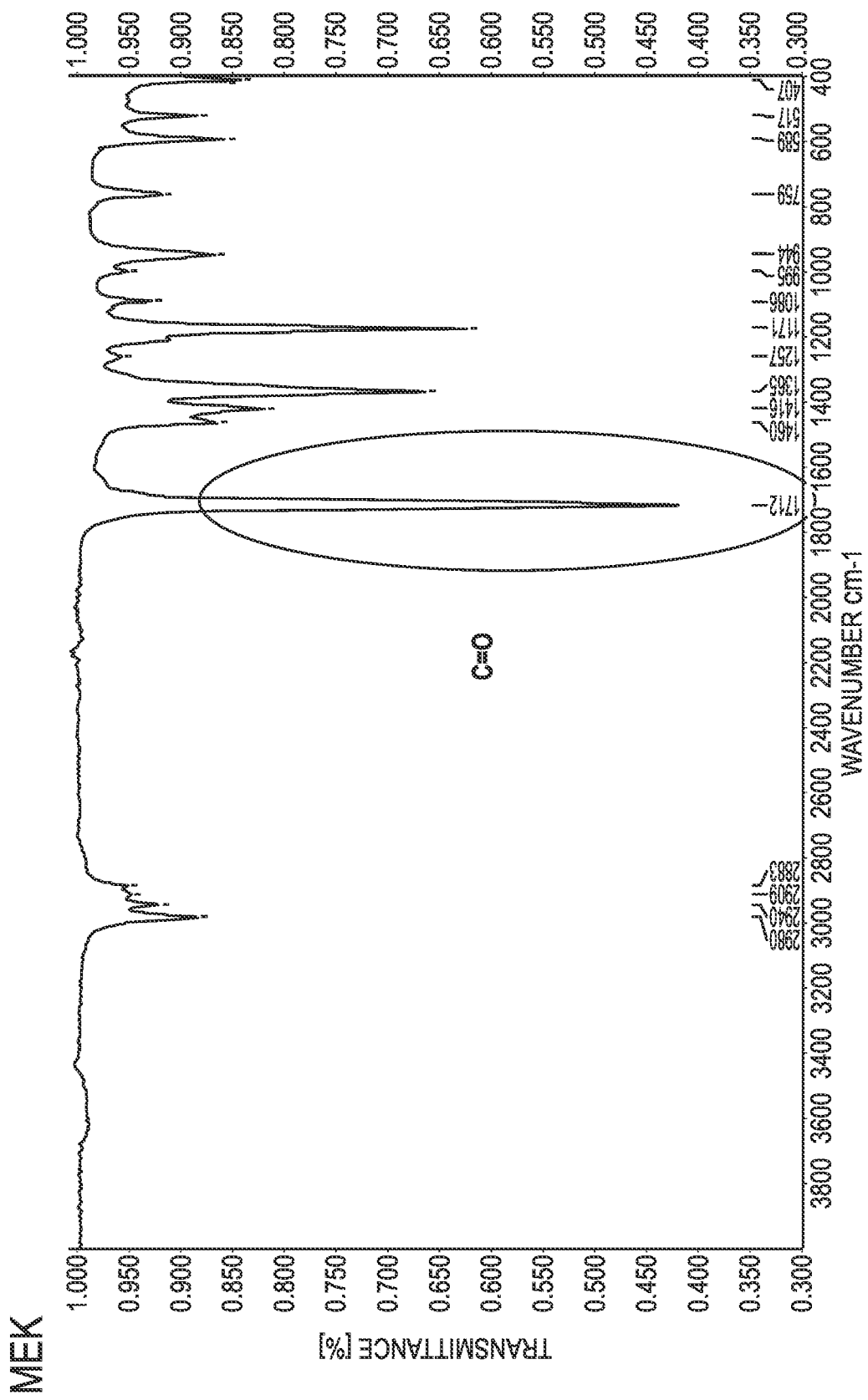
FIG. 14 shows the FTIR spectra of MEK.
Figure 15:
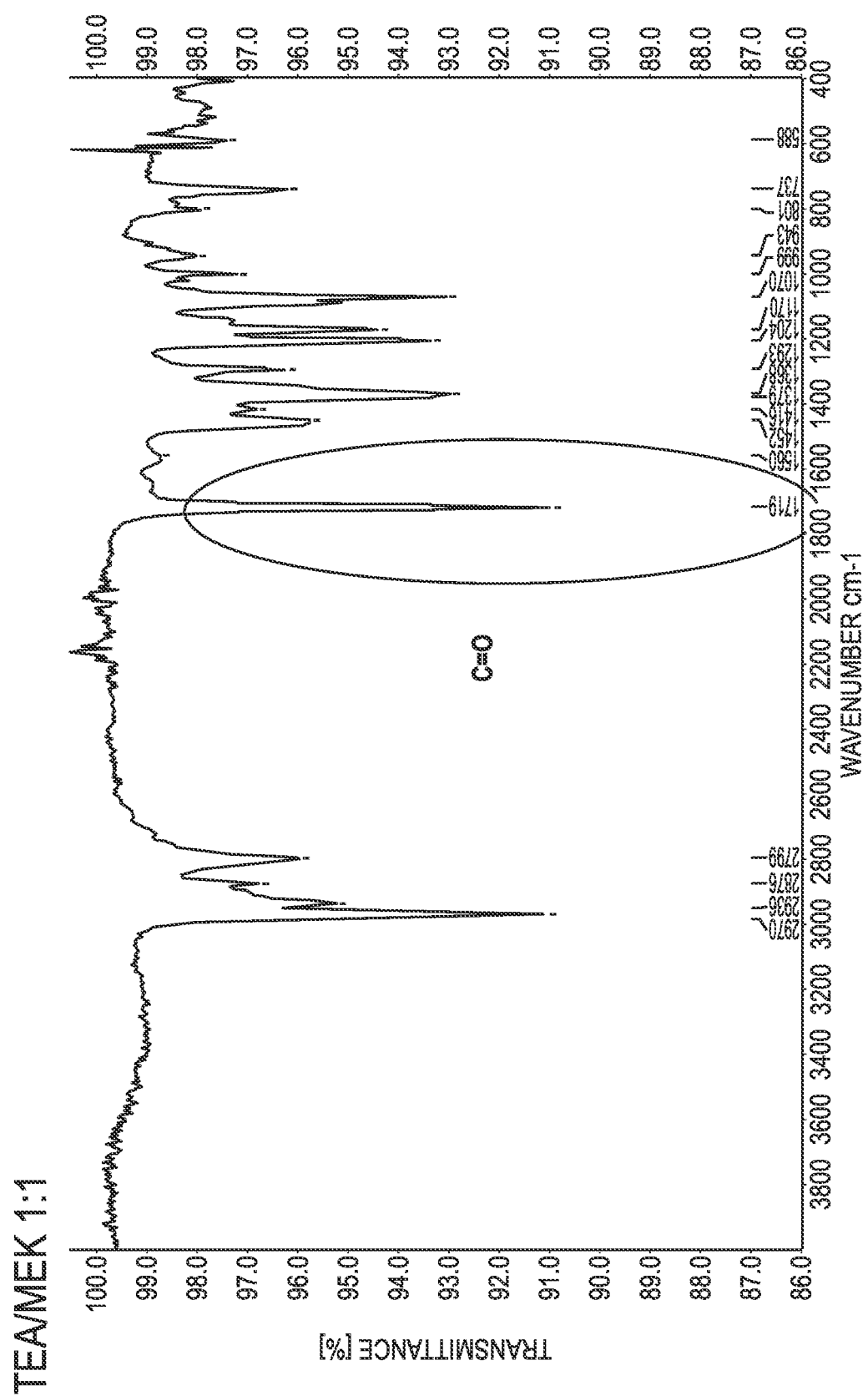
FIG. 15 shows the FTIR spectra of TEA/MEK in a 1:1 molar ratio.
Figure 16:
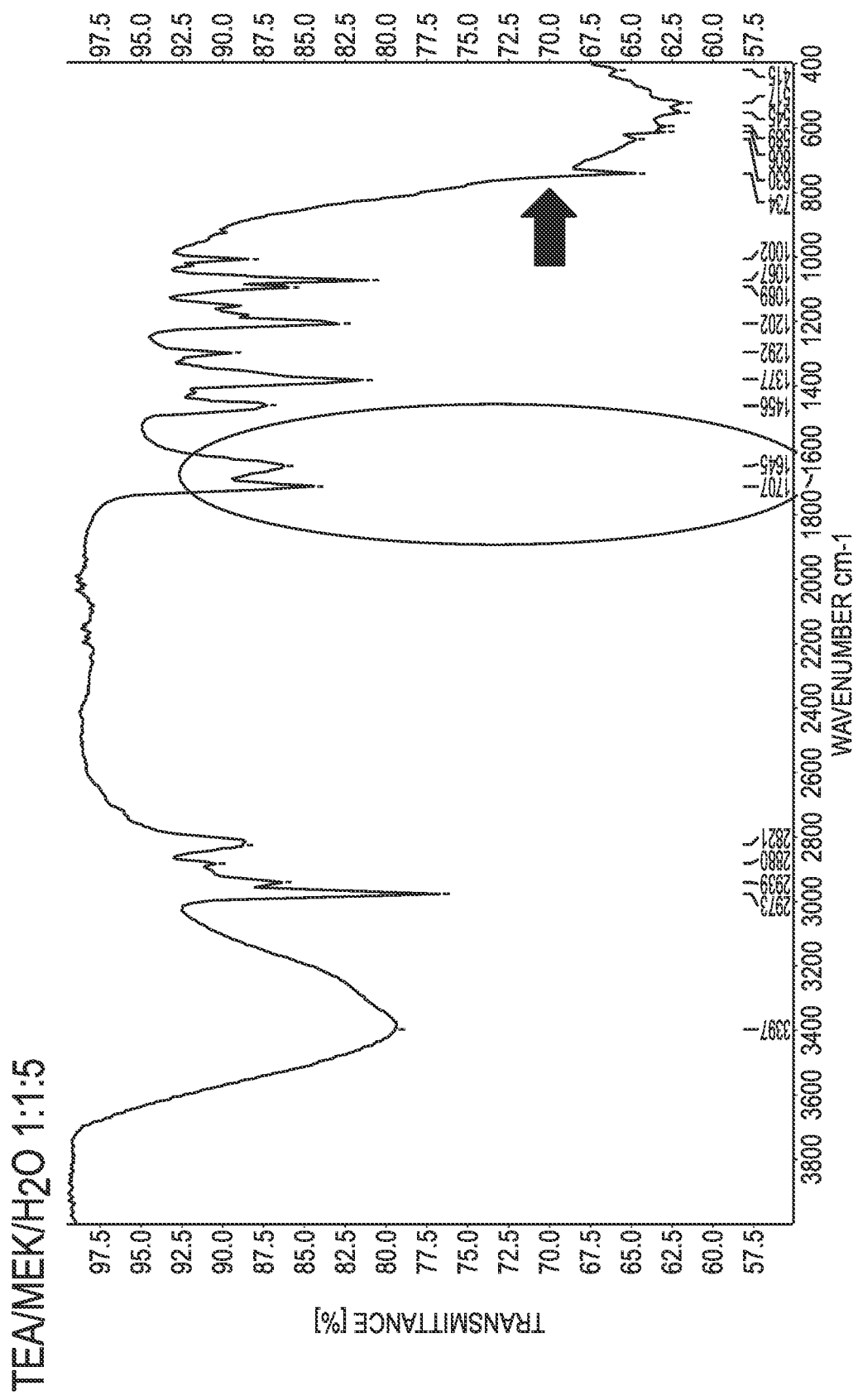
FIG. 16 shows the FTIR spectra of TEA/MEK/water in a 1:1:5 molar ratio.

| Draw | Feed | Ratio (amine-ketone) | Draw Conc | Duration | Sampling frequency | Average flux (l/h/m²) |
|---|---|---|---|---|---|---|
| TEA - MEK | Deionised Water 150 mM NaCl aq. | 0.5-1.0 | 10 and 20% | 1 h 40 min | 10 minutes | See FIG. 11 See FIG. 11 |
| TEA - CP | Deionised Water 150 mM NaCl aq. | 0.5-1.0 | 10 and 20% | 1 h 40 min | 10 minutes | See FIG. 12 See FIG. 12 |
| TEA - CP | Deionised Water | 0.5-1.0 | 5% | 1 h | 10 minutes | 1.63 |
| TEA- MEK | Deionised water | 1.0:1.0 | 100% | 1 h 40 mm | 10 minutes | 3.733 |

CP = cyclopentanone

It can be seen from Table 15 and FIG. 11 and FIG. 12 that the average water flux was affected by temperature and draw solution concentration. The highest water flux rate was seen with a 1.0:1.0 ratio of TEA to MEK. In the case of TEA and MEK, as the temperature increased so did the water flux. As the draw solution concentration doubled the water flux dropped slightly. In contrast with the TEA cyclopentanone draw solution, the water flux increased when the draw solution concentration doubled.

FTIR Experiments

The draw solutions were analyzed using the FTIR spectrometer. Various ratios of MEK and TEA with water were measured using FTIR. The resulting spectra were then analysed using principal component analysis. The samples investigated were labelled as TEA, MEK, TEA:MEK and TEA:MEK:H$_2$O.

Samples were placed into a sample dish on a temperature control stage and analysed. FT-IR spectroscopy was performed using a Bruker Vertex 70 FT-IR spectrometer. Analysis of samples involved obtaining 16 scans to produce each spectrum and a spectral resolution of 0.4 cm$^{-1}$.

The resulting spectra are shown as FIG. 13, FIG. 14, FIG. 15 and FIG. 16. it can be seen that the carbonyl peak at around 1712-1719 cm$^{-1}$ is converted to an enol in the presence of water. The single carbonyl peak at 1712-1719 cm$^{-1}$ (see in FIG. 14 and FIG. 15) is spilt into a double peak at 1645-1701 cm$^{-1}$ representing the enol form.

It is to be appreciated that these solutions that exhibit thermo-responsiveness have applicability as draw solutions in osmotic processes. It is to be appreciated that a thermo-responsive solution of the present invention could be used as a draw solution in osmotic processes as illustrated in FIG. 1 and FIG. 6. The draw solution can be used, for example, to draw water that requires purification through a semi-permeable membrane into the draw solution. Once the draw solution has reached its osmotic potential the draw solution mixture can be heated to its lower critical solution temperature at which point the ketone and amine mixture becomes immiscible in the water solution and the purified/treated water solution can be readily separated (by physical or mechanical separation in a very energy efficient manner) from the draw solution. The draw solution can be recycled and reused in a further osmotic cycle. It is to be appreciated that the lower critical solution temperature can be varied depending on the ketone/amine mix and whether one or more ketones or amines are used. For energy efficient purposes it would be desirable to have a lower critical solution temperature that is not much higher than room temperature.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to combinations, kits, compounds, means, methods, and/or steps disclosed herein.

Accordingly, one of ordinary skill in the art will readily appreciate from the disclosure that later modifications, substitutions, and/or variations performing substantially the same function or achieving substantially the same result as embodiments described herein may be utilised according to such related embodiments of the present invention. Thus, the invention is intended to encompass, within its scope, the modifications, substitutions, and variations to processes, manufactures, compositions of matter, compounds, means, methods, and/or steps disclosed herein.

The invention claimed is:

1. A thermo-responsive osmotic solution having a lower critical solution temperature in a solvent, the thermo-responsive osmotic solution comprising:
   a) at least one tertiary amine containing compound selected from:

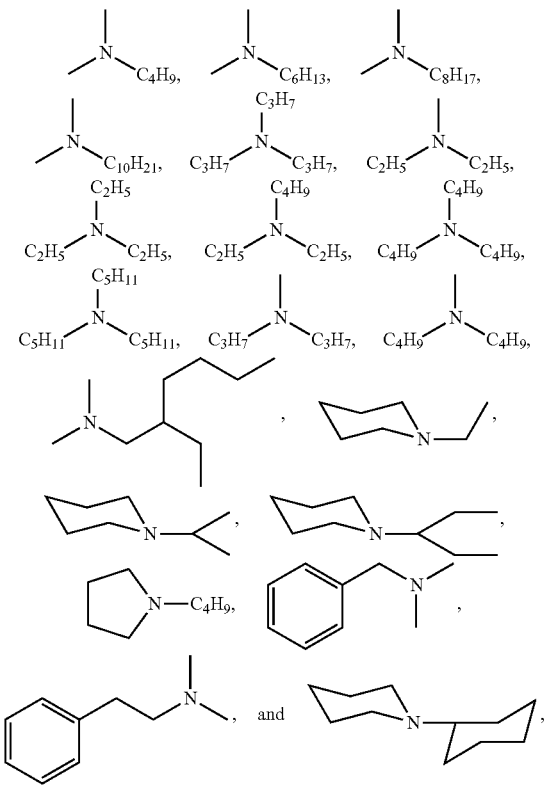

and
   b) at least one enolisable carbonyl compound selected from acetone, acetophenone, methylethylketone (2-butanone), cyclohexanone, cyclopentanone, 2-propanone, 2-pentanone, 3-pentanone, 4-methyl-2-pentanone, 2-octanone and 3-methyl-2-butanone, or a combination thereof;
   wherein the at least one tertiary amine containing compound or the at least one enolisable carbonyl compound is immiscible with the solvent at or above 20 degrees Celsius and at 1 atmosphere; and
   wherein the solvent is water.

2. The solution as claimed in claim 1, wherein the solution comprises a combination of more than one tertiary amine containing compound.

3. The solution as claimed in claim 1, wherein the at least one tertiary amine containing compound in the solution is immiscible with the solvent at or above 20 degrees Celsius and at 1 atmosphere.

4. The solution as claimed in claim 1, wherein the at least one tertiary amine containing compound is N(C$_1$-C$_7$ alkyl)$_3$.

5. The solution as claimed in claim 1, wherein the at least one tertiary amine containing compound is N(C$_1$-C$_4$ alkyl)$_3$.

6. The solution as claimed in claim 1, wherein the at least one tertiary amine containing compound is N(C$_2$ alkyl)$_3$ (triethylamine).

7. The solution as claimed in claim 1, wherein the molar ratio of the at least one tertiary amine containing compound to the at least one enolisable carbonyl compound of Formula I is about 1:5 or 5:1.

8. The solution as claimed in claim 1, wherein the molar ratio of the at least one tertiary amine containing compound to the at least one enolisable carbonyl compound of Formula I is about 1:3 or 3:1.

9. The solution as claimed in claim 1, wherein the molar ratio of the at least one tertiary amine containing compound to the at least one enolisable carbonyl compound of Formula I is about 1:2 or 2:1.

10. The solution as claimed in claim 1, wherein the molar ratio of the at least one tertiary amine containing compound to the at least one enolisable carbonyl compound of Formula I is about 1:1.

11. The solution as claimed in claim 1, wherein the at least one tertiary amine containing compound is triethylamine and the enolisable carbonyl is methylethylketone (2-butanone).

12. The solution as claimed in claim 11, wherein the molar ratio of the triethylamine to methylethylketone (2-butanone) is 1:2.

13. The solution as claimed in claim 12, wherein the molar ratio of the triethylamine to methylethylketone (2-butanone) is 1:2.

14. A thermo-responsive osmotic solution having a lower critical solution temperature in a solvent, the thermo-responsive osmotic solution comprising triethylamine and methylethylketone (2-butanone), wherein the triethylamine or the methylethylketone (2-butanone) is immiscible with the solvent at or above 20 degrees Celsius and at 1 atmosphere; and wherein the solvent is water.

* * * * *